(12) United States Patent
Muthusamy et al.

(10) Patent No.: US 11,149,017 B2
(45) Date of Patent: Oct. 19, 2021

(54) SOLID STATE FORMS OF APALUTAMIDE

(71) Applicant: WATSON LABORATORIES INC., Corona (CA)

(72) Inventors: Anantha Rajmohan Muthusamy, Sivakasi (IN); Sundara Lakshmi Kanniah, Vellore (IN); Nitin Dnyaneshwar Arote, Navimumbai (IN); Omkar Vilas Bhagwat, Thane (IN); Jitendra Kamalakar Sonar, Tal-Shahada (IN); Vitthal Baburao Poundkar, Kolhapur (IN); Yogesh Dhananjay Wagh, Thane (IN)

(73) Assignee: WATSON LABORATORIES INC., Corona, CA (US)

(*) Notice: Subject to any disclaimer, the term of this patent is extended or adjusted under 35 U.S.C. 154(b) by 0 days.

(21) Appl. No.: 16/468,912

(22) PCT Filed: Dec. 13, 2017

(86) PCT No.: PCT/US2017/066021
§ 371 (c)(1),
(2) Date: Jun. 12, 2019

(87) PCT Pub. No.: WO2018/112001
PCT Pub. Date: Jun. 21, 2018

(65) Prior Publication Data
US 2019/0322640 A1    Oct. 24, 2019

(30) Foreign Application Priority Data

Dec. 13, 2016  (IN) ............................ 201611042535
Jan. 17, 2017   (IN) ............................ 201711001778
Mar. 30, 2017  (IN) ............................ 201711011318

(51) Int. Cl.
*C07D 401/04*    (2006.01)

(52) U.S. Cl.
CPC ........ *C07D 401/04* (2013.01); *C07B 2200/13* (2013.01)

(58) Field of Classification Search
CPC .......................... C07D 401/04; C07B 2200/13
USPC ...................................................... 546/274.1
See application file for complete search history.

(56) References Cited

U.S. PATENT DOCUMENTS 8,445,507 B2    5/2013   Jung et al.

FOREIGN PATENT DOCUMENTS

| WO | WO-2008119015 A2 * | 10/2008 | ........... C07C 209/36 |
| WO | WO-2011103202 A2 * | 8/2011 | ........... A61K 31/506 |
| WO | 2013184681 A1 | 12/2013 | |
| WO | WO-2013184681 A1 * | 12/2013 | ............. A61P 13/08 |
| WO | WO-2014190895 A1 * | 12/2014 | ........... C07D 401/04 |
| WO | 2015166274 A1 | 11/2015 | |
| WO | 2016124149 A1 | 8/2016 | |

OTHER PUBLICATIONS

International Search Report for International Application No. PCT/US2017/066021, International Filing Date Dec. 13, 2017, dated May 4, 2018, 8 pages.
Written Opinion for International Application No. PCT/US2017/066021, International Filing Date Dec. 13, 2017, dated May 4, 2018, 9 pages.
Caira, Mino R.; "Crystalline Polymorphism of Organic Compounds"; Topics in Current Chemistry, vol. 198: 1998; pp. 163-208.

* cited by examiner

*Primary Examiner* — Rita J Desai
(74) *Attorney, Agent, or Firm* — Cantor Colburn LLP

(57) ABSTRACT

Disclosed are solid state forms of Apalutamide and salts thereof, processes for preparation thereof and pharmaceutical compositions thereof.

18 Claims, 10 Drawing Sheets

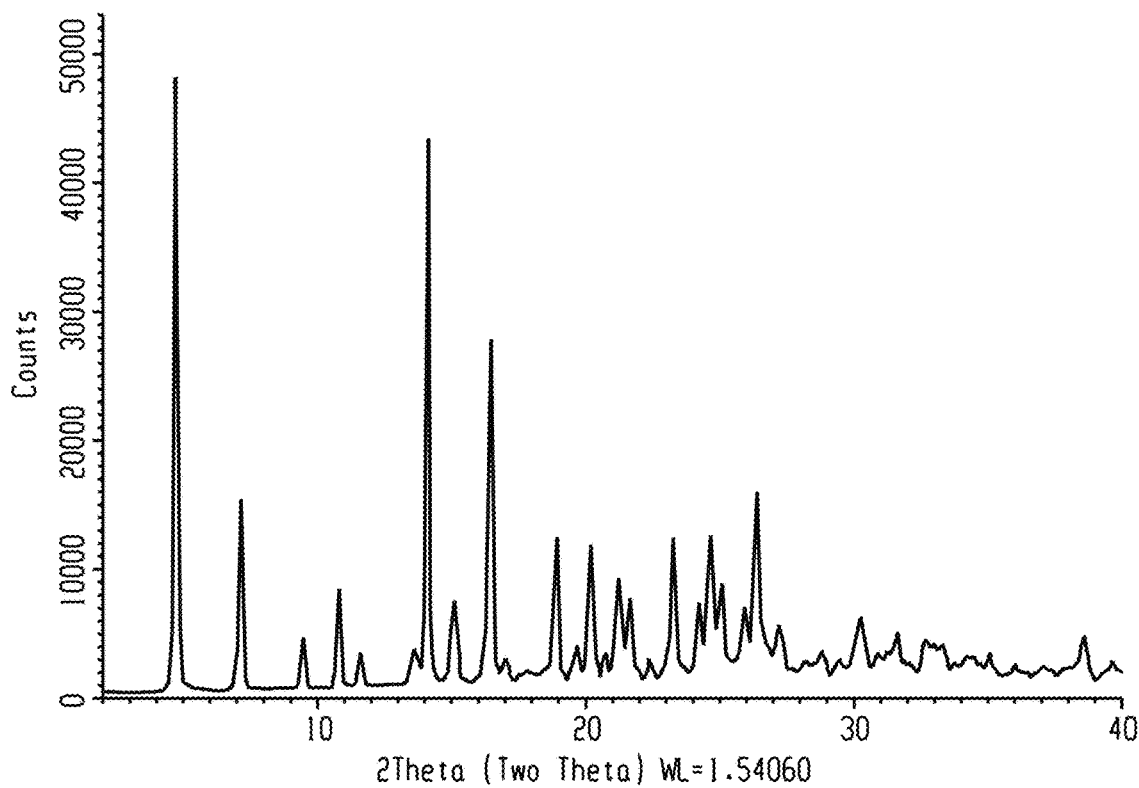
Fig. 1 PXRD pattern of Apalutamide form T1
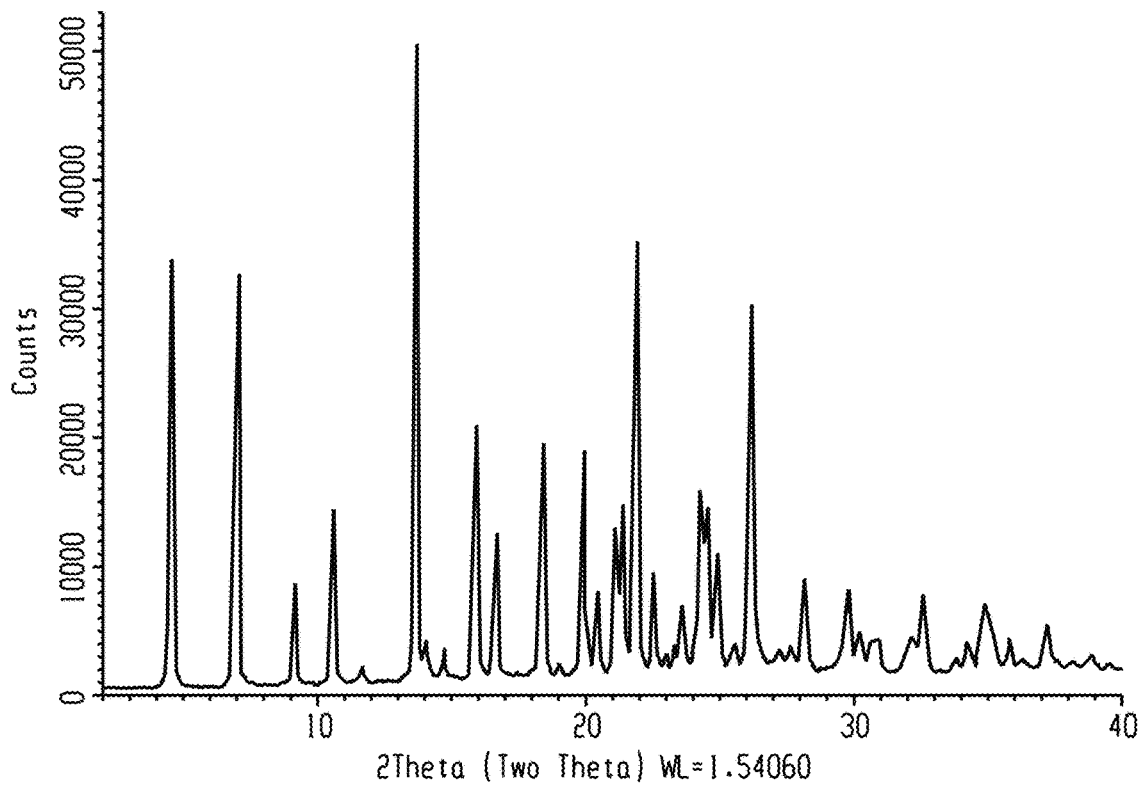
Fig. 2 PXRD pattern of Apalutamide form T2

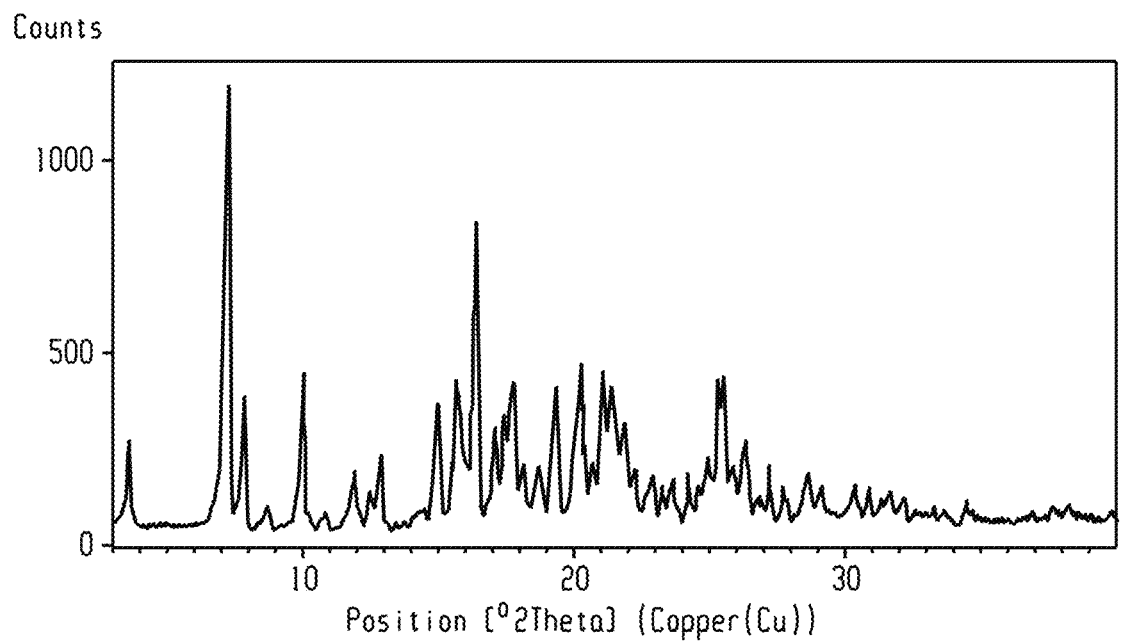
Fig. 3 PXRD pattern of Apalutamide form T3
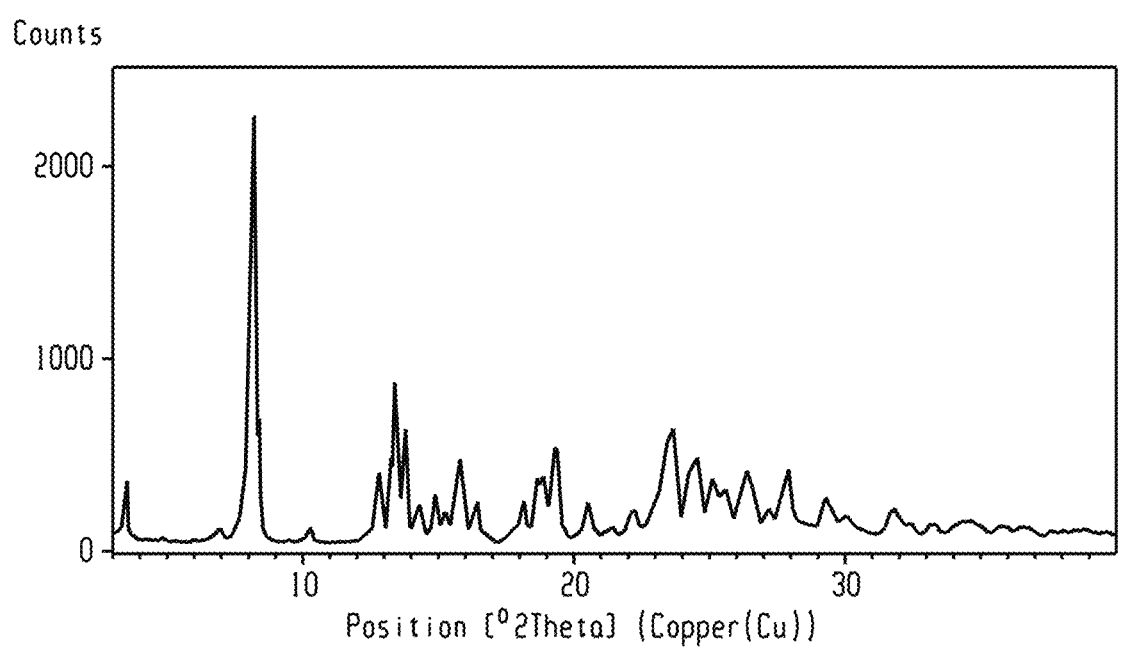
Fig. 4 PXRD pattern of Apalutamide form T4

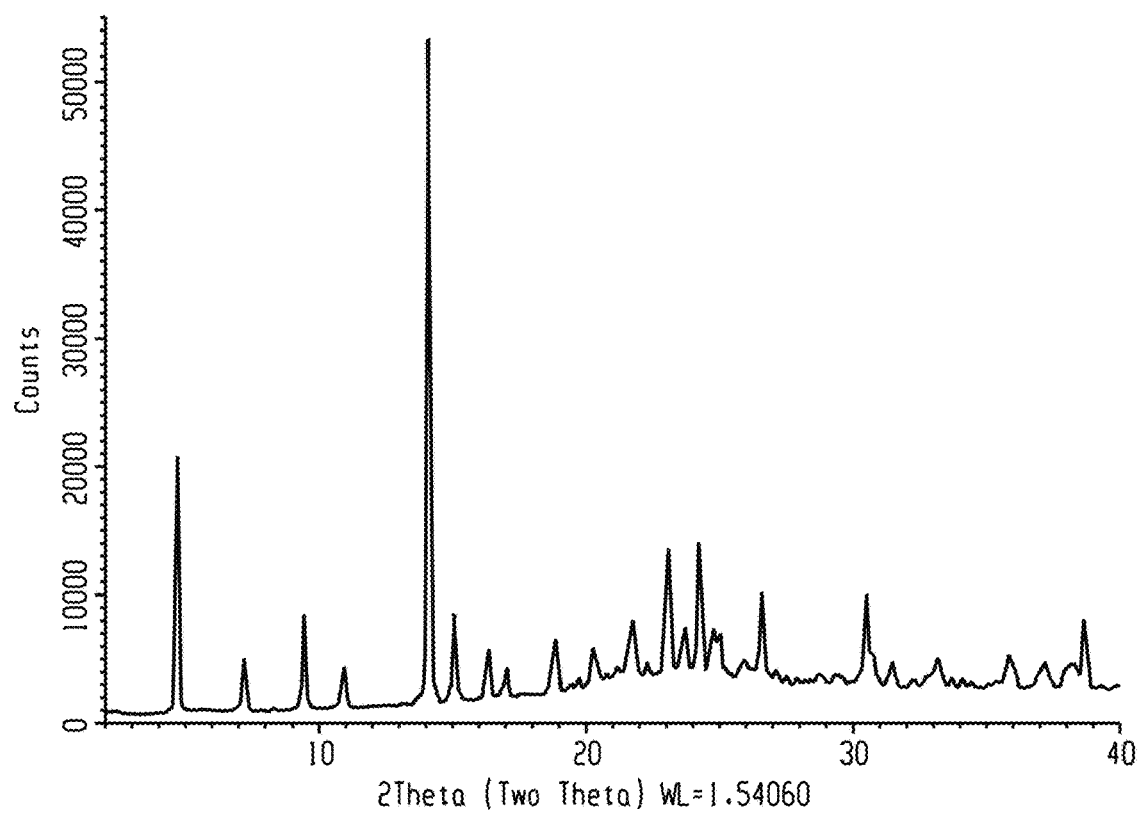
Fig. 5 PXRD pattern of Apalutamide form T5
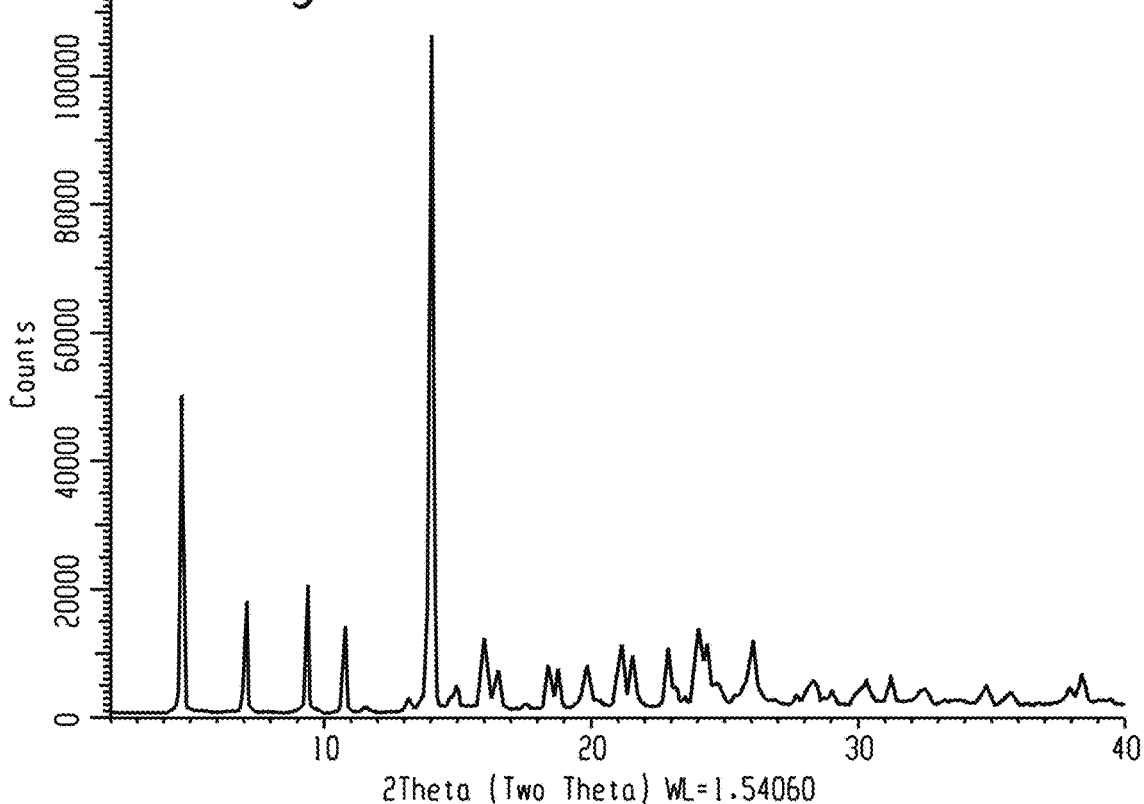
Fig. 6 PXRD pattern of Apalutamide form T6

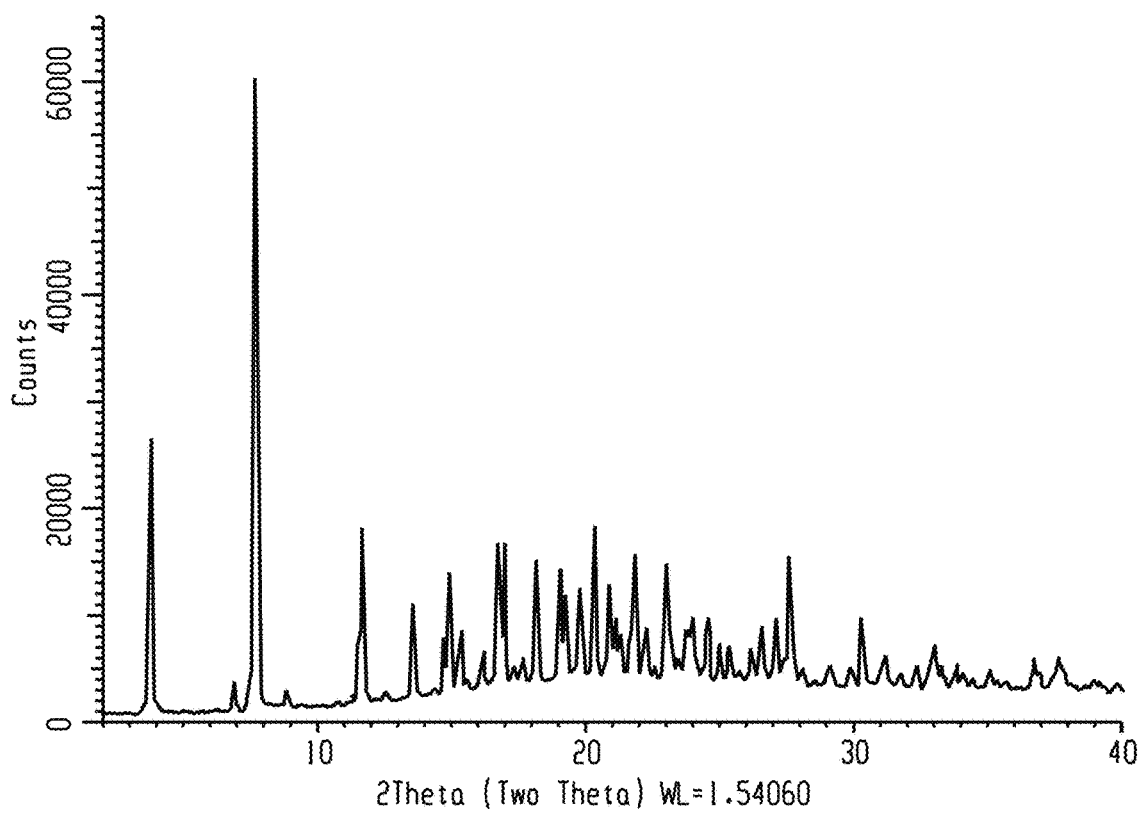
Fig. 7 PXRD pattern of Apalutamide form T7
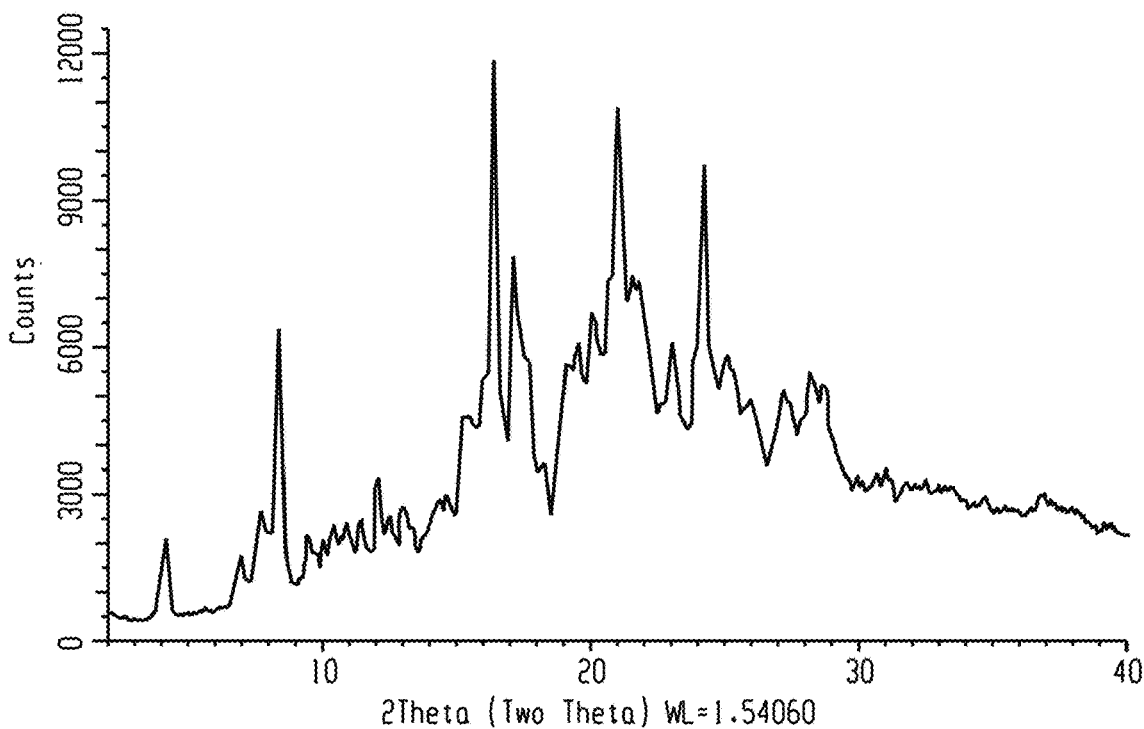
Fig. 8 PXRD pattern of Apalutamide form T8

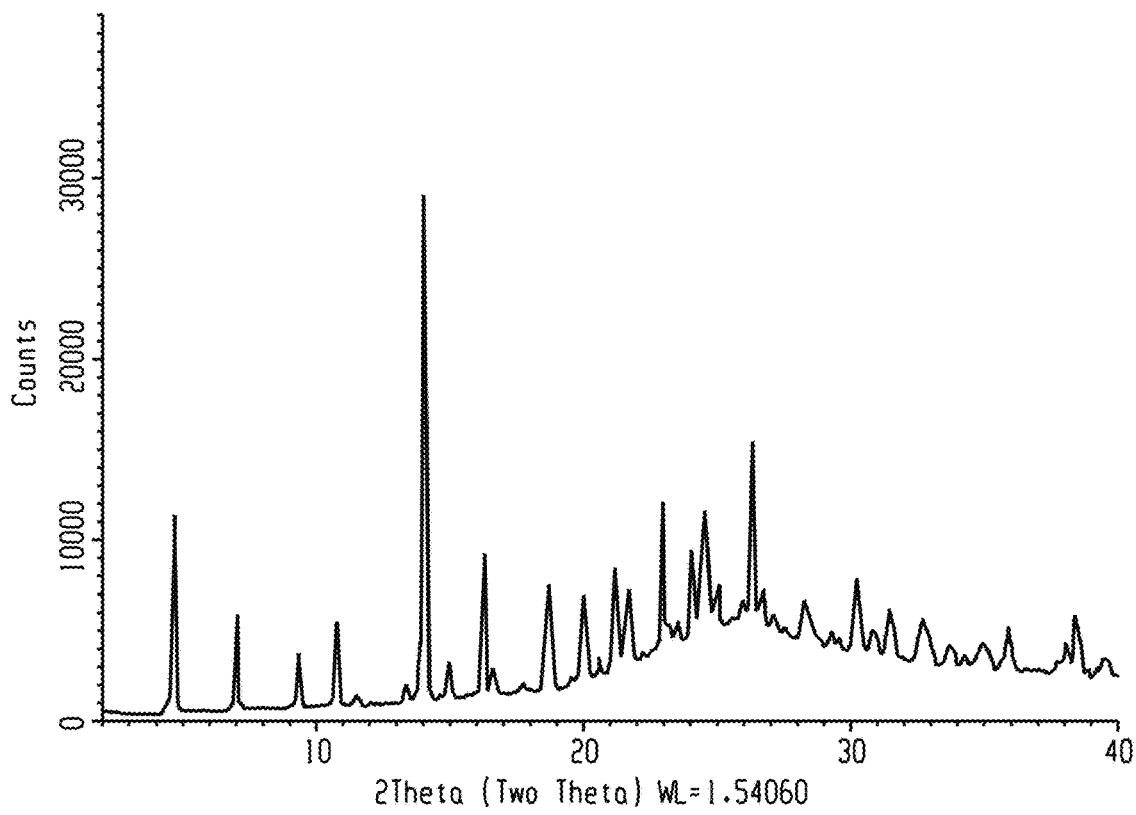
Fig. 9 PXRD pattern of Apalutamide form T9
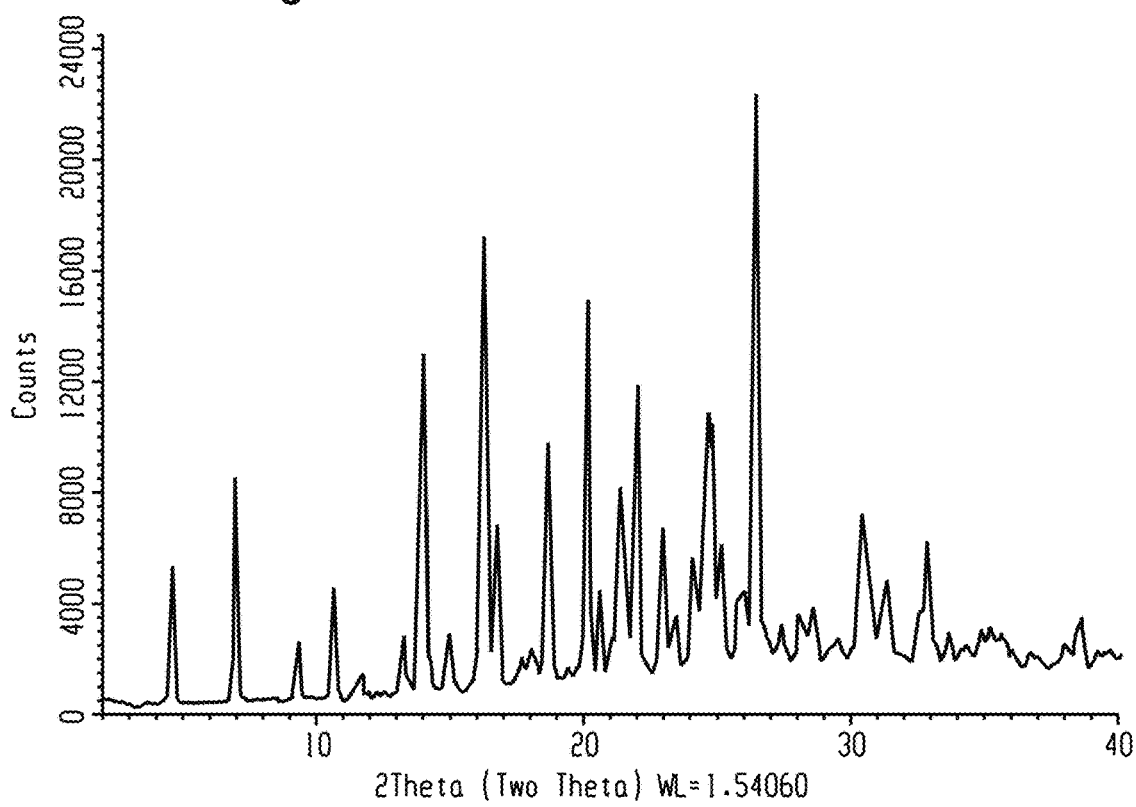
Fig. 10 PXRD pattern of Apalutamide form T10

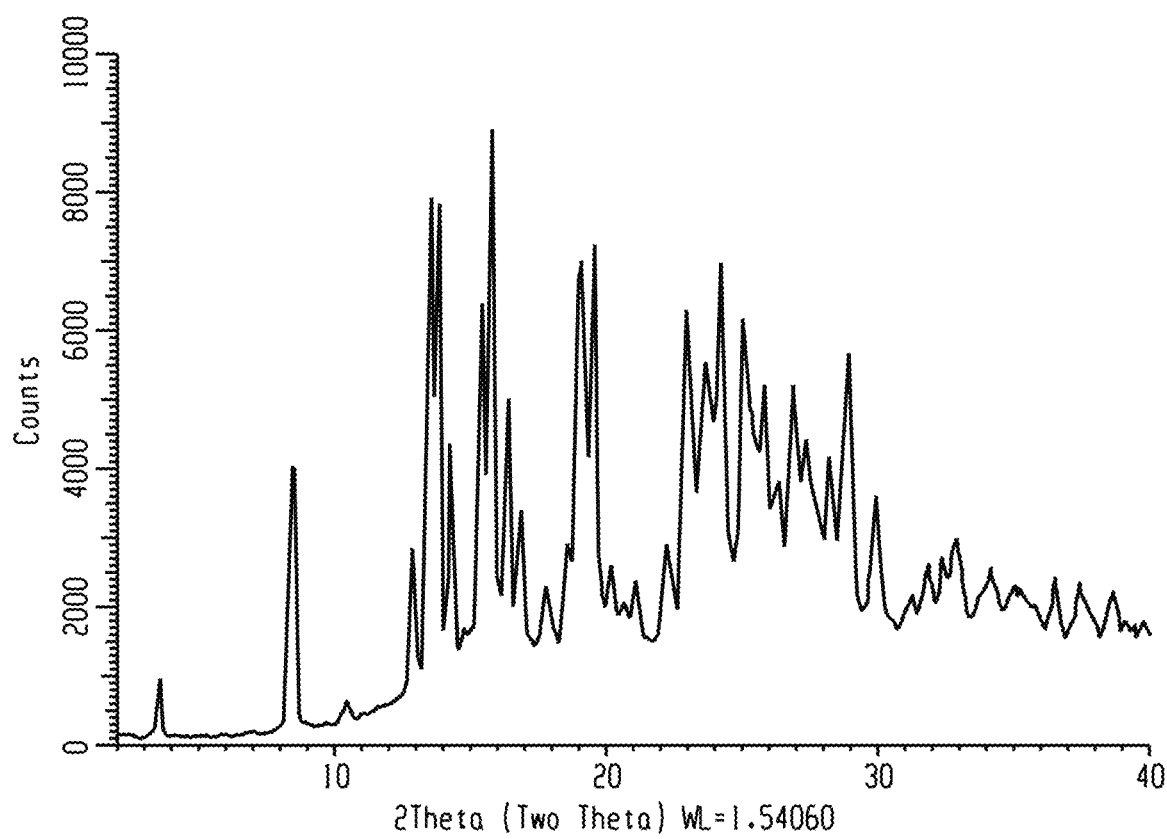
Fig. 11 PXRD pattern of Apalutamide form T11
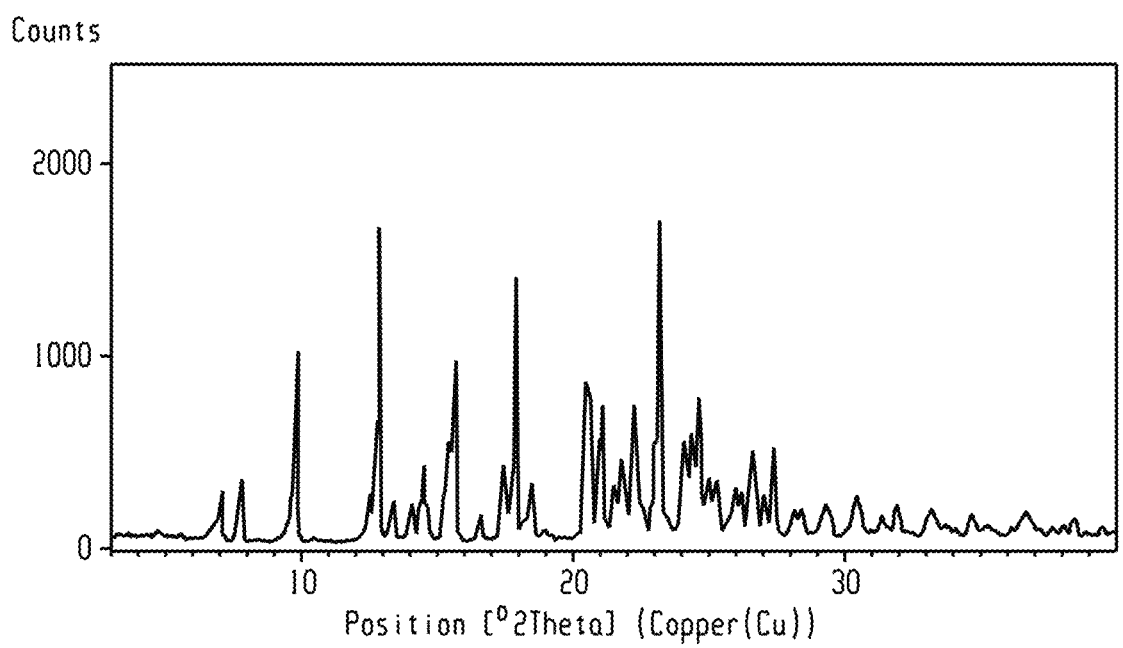
Fig. 12 PXRD pattern of Apalutamide form T12

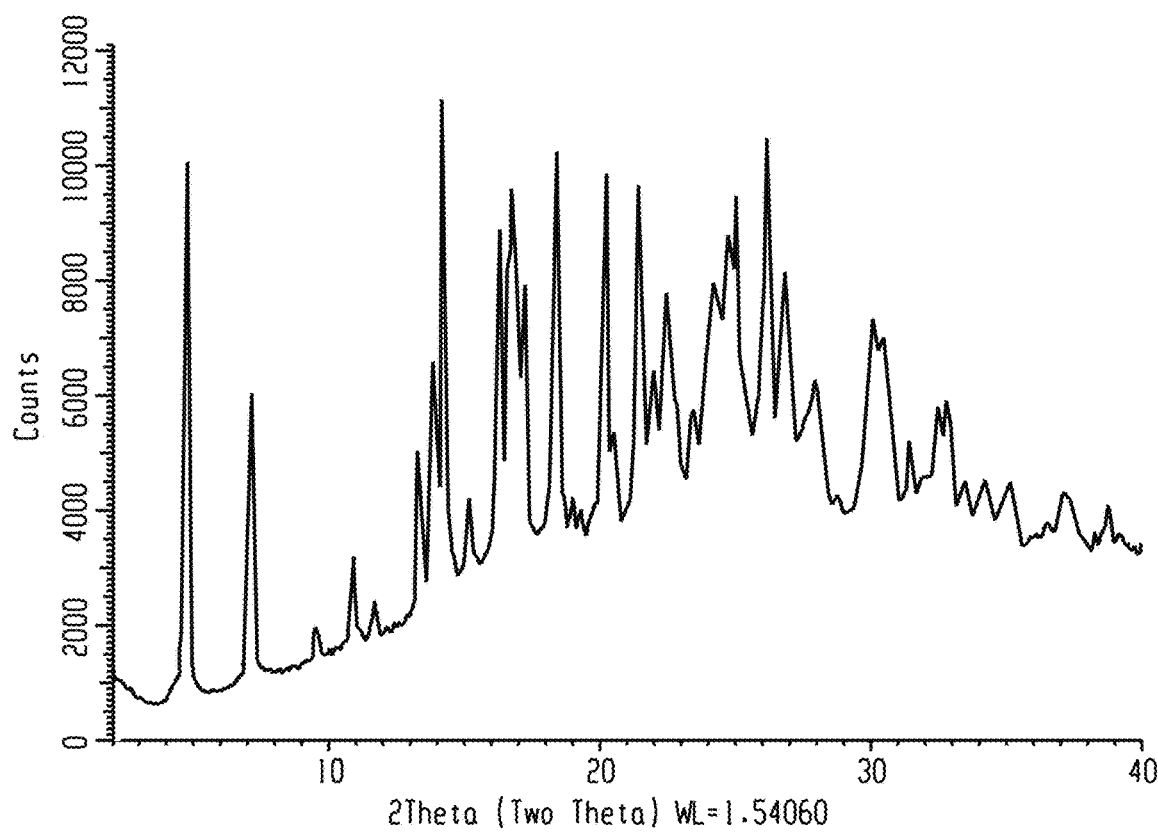
Fig. 13 PXRD pattern of Apalutamide form T13
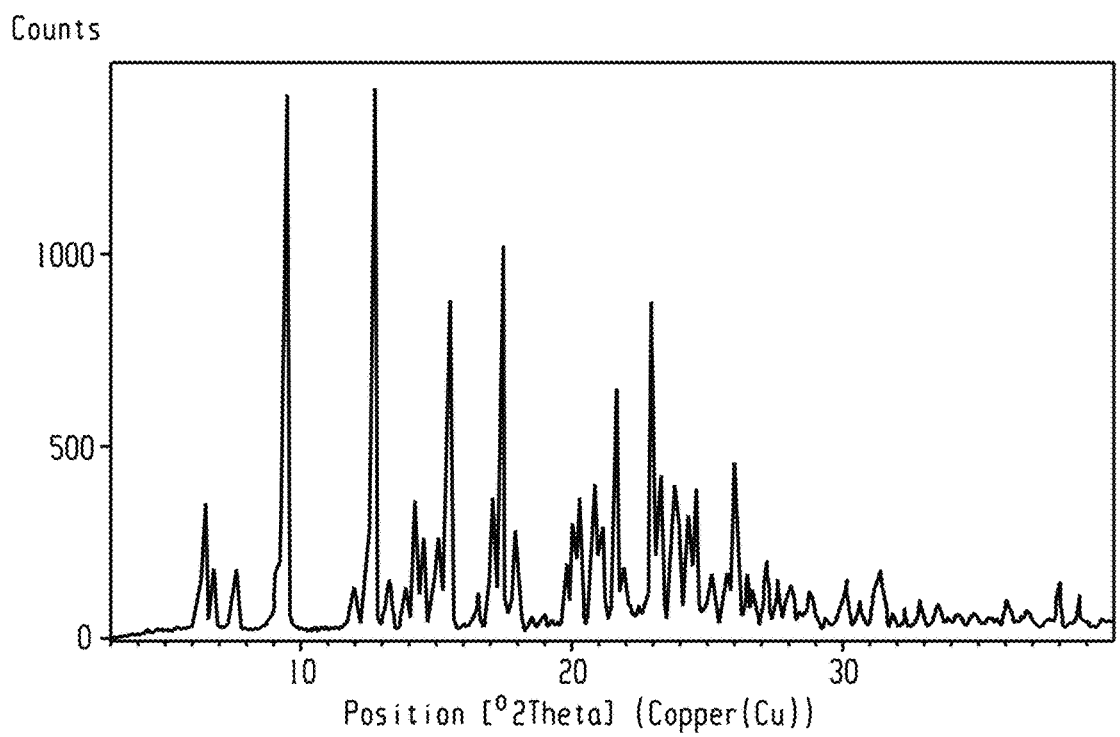
Fig. 14 PXRD pattern of Apalutamide form T14

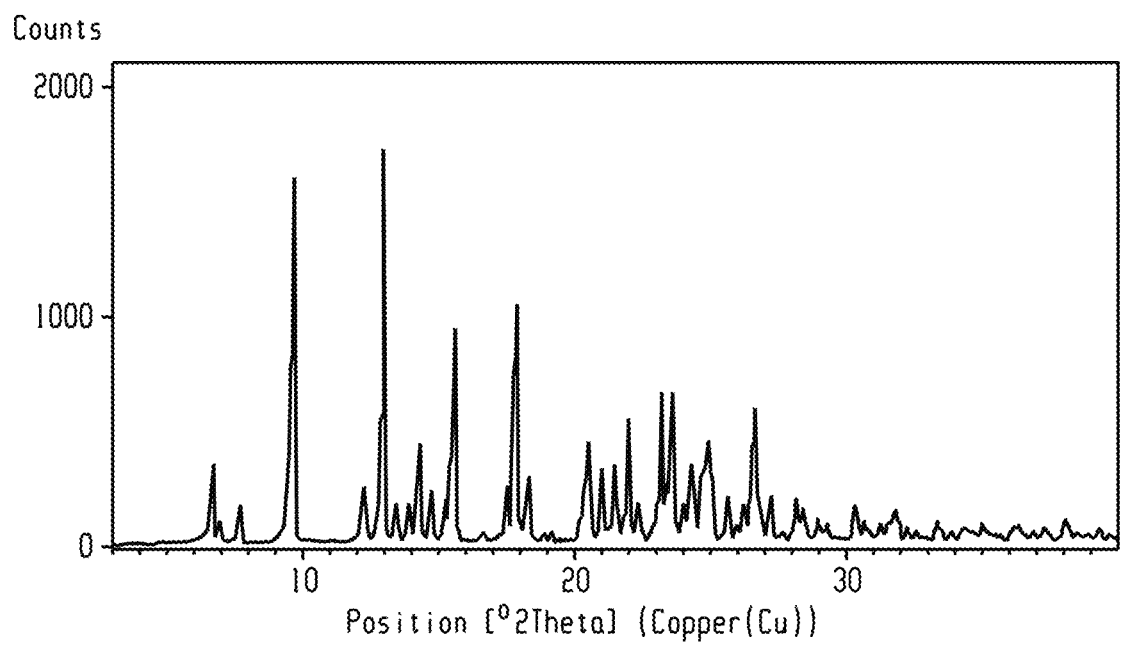
Fig. 15 PXRD pattern of Apalutamide form T15
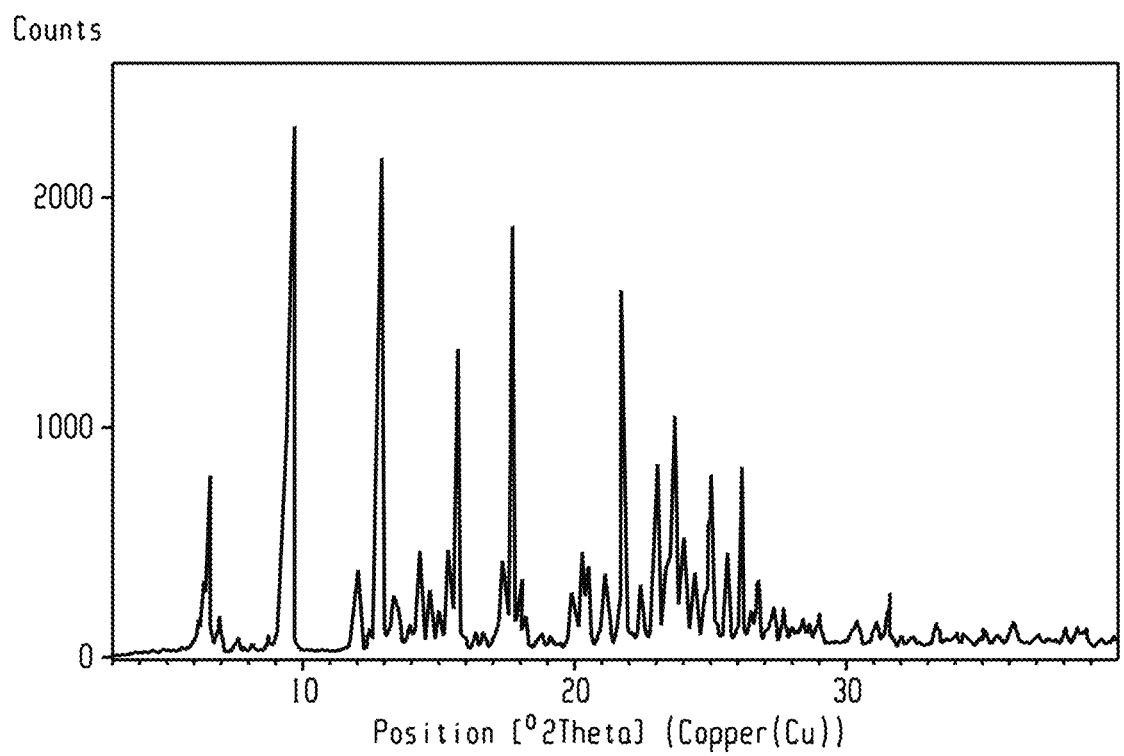
Fig. 16 PXRD pattern of Apalutamide form T16

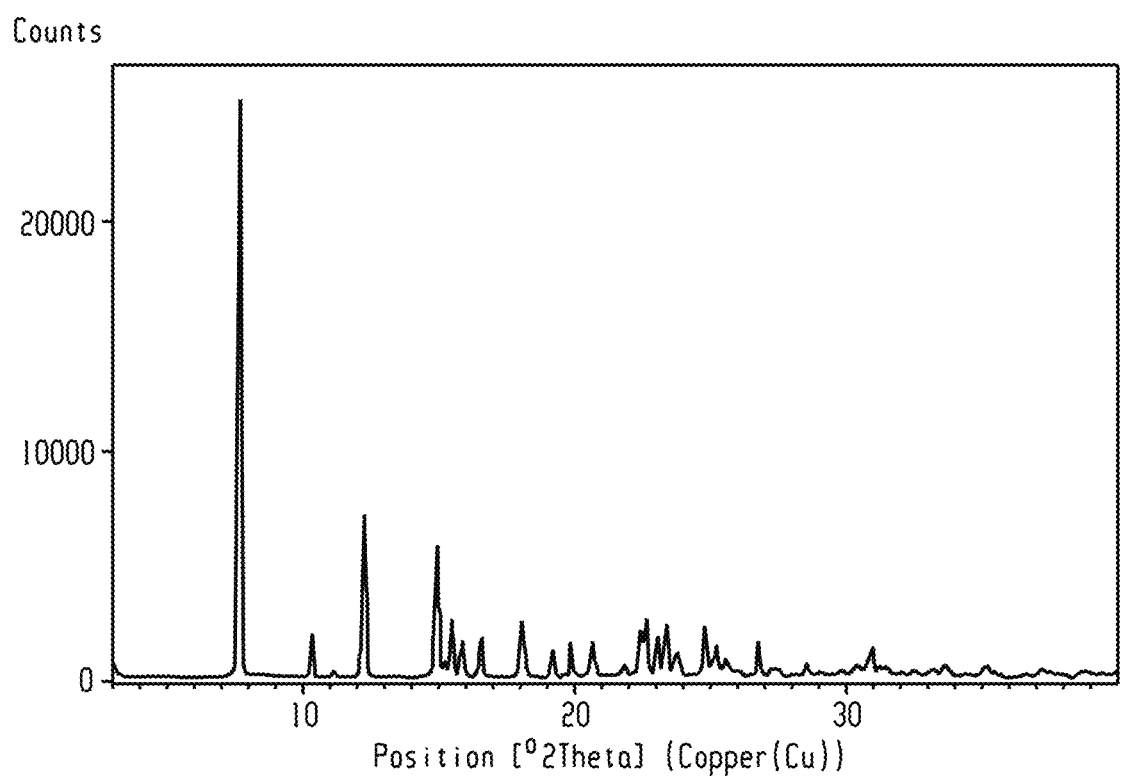
Fig. 17  PXRD pattern of Apalutamide form T17
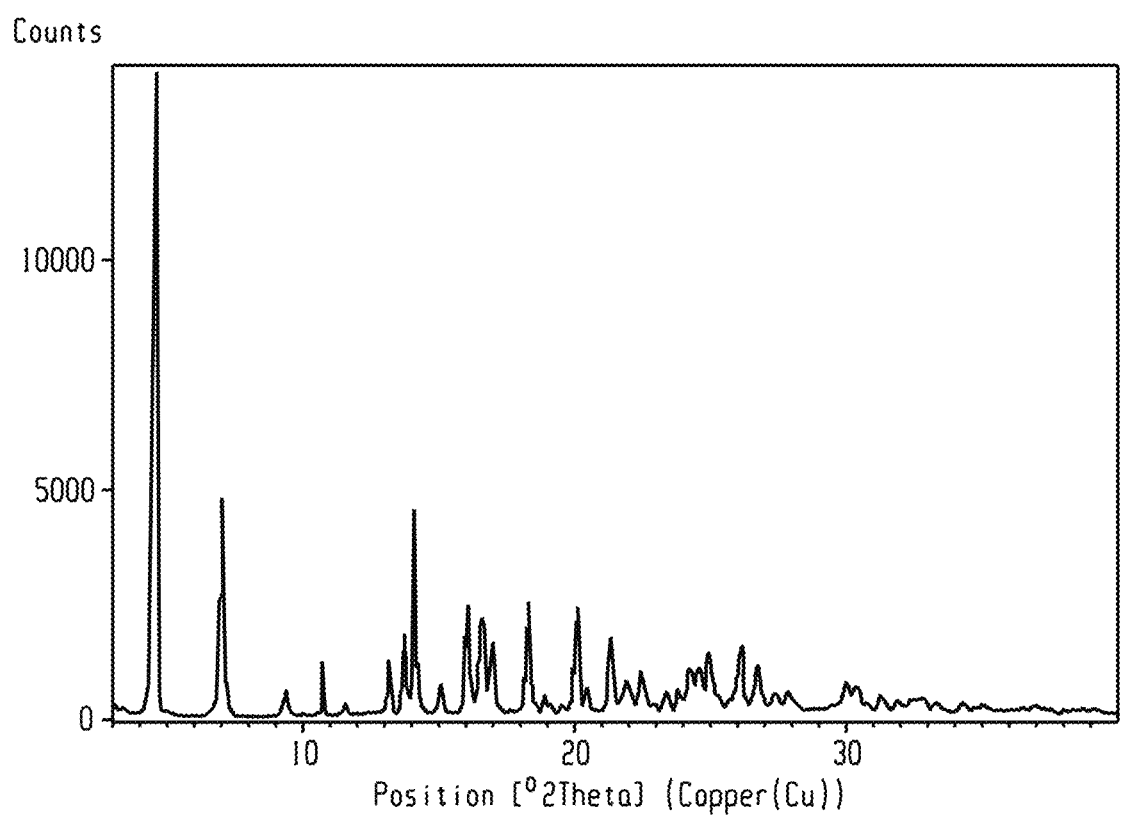
Fig. 18  PXRD pattern of Apalutamide form T13

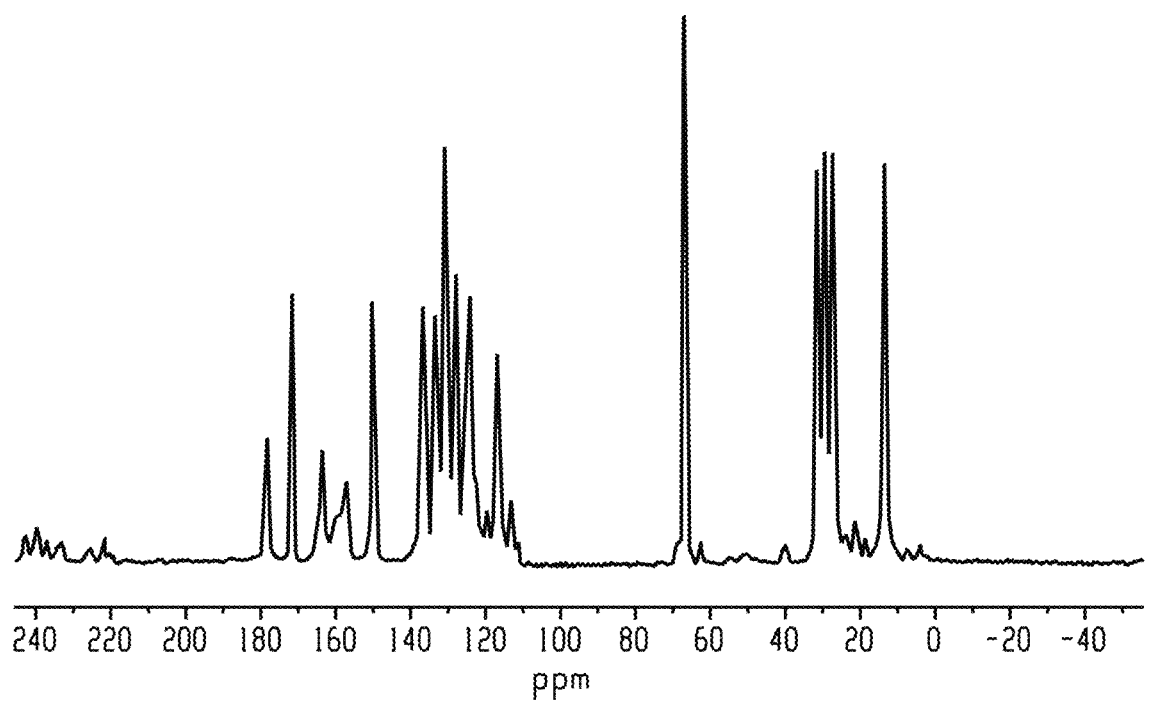
Fig. 19 A solid state $^{13}$C NMR spectrum of Apalutamide form T1

SOLID STATE FORMS OF APALUTAMIDE

CROSS-REFERENCE TO RELATED APPLICATIONS

This application is a National Stage application of PCT/US2017/066021, filed Dec. 13, 2017, and is related to, and claims the benefit of priority of, IN Application No. 201611042535 filed on Dec. 13, 2016, IN Application No. 201711001778 filed on Jan. 17, 2017, and IN Application No. 201711011318 filed on Mar. 30, 2017, the contents of each are incorporated herein by reference in their entirety for all purposes.

FIELD OF THE INVENTION

The present disclosure relates to solid state forms of Apalutamide and salts thereof, processes for preparation thereof and pharmaceutical compositions thereof.

BACKGROUND OF THE INVENTION

Apalutamide has the chemical name 4-[7-[6-cyano-5-(trifluoromethyl)pyridin-3-yl]-8-oxo-6-thioxo-5,7-diazaspiro[3.4]octan-5-yl]-2-fluoro-N-methylbenzamide. Apalutamide has the following chemical structure:

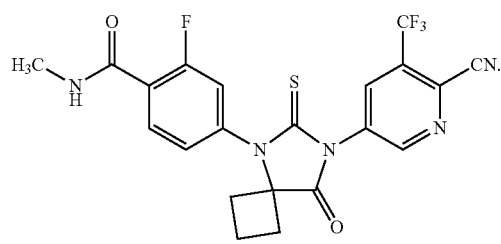 [SMILES: CNC(=O)c1ccc(N2C(=S)N(c3cnc(C#N)c(C(F)(F)F)c3)C(=O)C23CCC3)cc1F]

Apalutamide is an androgen receptor antagonist, under investigation for treatment of prostate cancer.

Apalutamide is disclosed in U.S. Pat. No. 8,445,507.

Crystalline forms of Apalutamide are described in WO2013184681 and WO2016124149.

Polymorphism, the occurrence of different crystal forms, is a property of some molecules and molecular complexes. A single compound, like Apalutamide, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

For at least these reasons, there is a need for solid state forms (including solvated forms) of Apalutamide and salts thereof.

SUMMARY OF THE INVENTION

The present disclosure relates to solid state forms of Apalutamide, to processes for preparation thereof, and to pharmaceutical compositions comprising these solid state forms.

The present disclosure also provides uses of the solid state forms of Apalutamide for preparing other solid state forms of Apalutamide, Apalutamide salts and solid state forms thereof.

In another embodiment, the present disclosure encompasses the above described solid state forms of Apalutamide for use in the preparation of pharmaceutical compositions and/or formulations, preferably for the treatment of prostate cancer.

In another embodiment the present disclosure encompasses the use of the above described solid state form of Apalutamide for the preparation of pharmaceutical compositions and/or formulations.

The present disclosure further provides pharmaceutical compositions comprising any one or a combination of the solid state forms of Apalutamide according to the present disclosure.

In yet another embodiment, the present disclosure encompasses pharmaceutical formulations comprising the above described solid state forms of Apalutamide and at least one pharmaceutically acceptable excipient, preferably for oral treatment in a form of tablets or capsules.

The present disclosure encompasses processes to prepare said pharmaceutical formulations of Apalutamide comprising combining any one or a combination of the above solid state forms and at least one pharmaceutically acceptable excipient.

The solid state forms as defined herein, as well as the pharmaceutical compositions or formulations of the solid state form of Apalutamide, can be used as medicaments, particularly for the treatment of prostate cancer.

The present disclosure also provides methods of treating cancer, in particular prostate cancer, comprising administering a therapeutically effective amount of any one or a combination of the solid state forms of Apalutamide of the present disclosure, or at least one of the above pharmaceutical compositions or formulations, to a subject suffering from cancer, in particular prostate cancer, or otherwise in need of the treatment.

The present disclosure also provides uses of the solid state forms of Apalutamide of the present disclosure, or at least one of the above pharmaceutical compositions or formulations for the manufacture of a medicament for treating cancer, in particular prostate cancer.

BRIEF DESCRIPTION OF THE FIGURES

FIG. 1 shows a powder X-ray diffraction pattern ("powder XRD" or "PXRD") of Apalutamide form T1.

FIG. 2 shows a powder X-ray diffraction pattern of Apalutamide form T2.

FIG. 3 shows a powder X-ray diffraction pattern of Apalutamide form T3.

FIG. 4 shows a powder X-ray diffraction pattern of Apalutamide form T4.

FIG. 5 shows a powder X-ray diffraction pattern of Apalutamide form T5.

FIG. 6 shows a powder X-ray diffraction pattern of Apalutamide form T6.

FIG. 7 shows a powder X-ray diffraction pattern of Apalutamide form T7.

FIG. 8 shows a powder X-ray diffraction pattern of Apalutamide form T8.

FIG. 9 shows a powder X-ray diffraction pattern of Apalutamide form T9.

FIG. 10 shows a powder X-ray diffraction pattern of Apalutamide form T10.

FIG. 11 shows a powder X-ray diffraction pattern of Apalutamide form T11.

FIG. 12 shows a powder X-ray diffraction pattern of Apalutamide form T12.

FIG. 13 shows a powder X-ray diffraction pattern of Apalutamide form T13.

FIG. 14 shows a powder X-ray diffraction pattern of Apalutamide form T14.

FIG. 15 shows a powder X-ray diffraction pattern of Apalutamide form T15.

FIG. 16 shows a powder X-ray diffraction pattern of Apalutamide form T16.

FIG. 17 shows a powder X-ray diffraction pattern of Apalutamide form T17.

FIG. 18 shows a powder X-ray diffraction pattern of Apalutamide form T13.

FIG. 19 shows a solid state $^{13}C$ NMR spectrum of Apalutamide form T1.

DETAILED DESCRIPTION OF THE INVENTION

The present disclosure relates to solid state forms of Apalutamide and salts thereof, processes for preparation thereof and pharmaceutical compositions comprising said solid state forms.

The solid state forms of Apalutamide according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Apalutamide and salts thereof referred to herein as being characterized by graphical data "as depicted in" a Figure will thus be understood to include any crystal forms of the Apalutamide and salts thereof, characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by PXRD. Thus, solid state of Apalutamide and salts thereof, described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state form of Apalutamide and salts thereof. Accordingly, in some embodiments of the disclosure, the described solid state forms of Apalutamide and salts thereof may contain from about 1% to about 20% (w/w), from about 5% to about 20% (w/w), or from about 5% to about 10% (w/w) of one or more other solid state forms of the same Apalutamide and salts thereof.

As used herein, unless stated otherwise, PXRD peaks reported herein are preferably measured using $CuK_\alpha$ radiation, $\lambda=1.5418$ Å.

As used herein, the term "isolated" in reference to solid state forms of Apalutamide and salts thereof, of the present disclosure corresponds to solid state forms of Apalutamide and salts thereof that are physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The crystal hydrate indicated by single crystal analysis or by water analysis by Karl Fischer (KF) titration or by TGA analysis of this product is believed to have been produced as a result of water introduced from the atmosphere in which this material was processed, or by traces of water present in the solvents that were in contact with the material, or a combination of these factors.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

As used herein, and unless stated otherwise, the term "anhydrous" in relation to crystalline Apalutamide relates to a crystalline Apalutamide which does not include any crystalline water (or other solvents) in a defined, stoichiometric amount within the crystal. Moreover, an "anhydrous" form does not contain more than 1% (w/w) of either water or organic solvents as measured for example by TGA.

As used herein, crystalline form A of Apalutamide is characterized as having XRPD pattern with characteristic peaks at 4.8±0.1 degrees 2-theta, 7.1±0.1 degrees 2-theta, 14.2±0.1 degrees 2-theta, 16.3±0.1 degrees 2-theta, 20.1±0.1 degrees 2-theta.

As used herein, crystalline form B of Apalutamide is characterized as having XRPD pattern with characteristic peaks at 12.1±0.1 degrees 2-theta, 16.0±0.1 degrees 2-theta, 16.7±0.1 degrees 2-theta, 20.1±0.1 degrees 2-theta, 20.3±0.1 degrees 2-theta.

The present disclosure comprises a crystalline form of Apalutamide designated as form T1. The crystalline form T1 of Apalutamide can be characterized by data selected from one or more of the following: a PXRD pattern having peaks at 11.4, 18.7, 19.5, 21.1, 21.5, 26.2, 27.1 and 30.1 degrees 2-theta±0.1 degrees 2-theta; a PXRD pattern as depicted in FIG. 1; or combinations of these data. Crystalline form T1 of Apalutamide may alternatively or additionally be characterized by data selected from one or more of the following: a solid state $^{13}$C NMR spectrum with peaks at 124.5, 128.5, 133.6, 137.0, and 157.6 ppm±0.2 ppm; or by a solid state $^{13}$C NMR spectrum having the following chemical shift absolute differences from a peak at 172.1 ppm±2 ppm of 47.6, 43.6, 38.5, 35.1 and 14.5 ppm±0.1 ppm; or by a solid state $^{13}$C NMR spectrum having the following chemical shift absolute differences from a peak at 157.6 ppm±1 ppm of 14.5 ppm±0.1 ppm; or by a solid state $^{13}$C NMR spectrum substantially as depicted in FIG. 19; or combinations of these data.

Crystalline form T1 of Apalutamide may be further characterized by the PXRD pattern having peaks at 11.4, 18.7, 19.5, 21.1, 21.5, 26.2, 27.1 and 30.1 degrees 2-theta±0.1 degrees 2-theta, and also having one, two, three, four or five additional peaks at 4.6, 7.0, 13.5, 14.0 and 16.8 degrees 2-theta±0.1 degrees 2-theta; and combinations of these data.

Crystalline form T1 of Apalutamide is a hydrate, in particular a monohydrate.

Crystalline form T1 of Apalutamide according to any of the above embodiments is a hydrate having about 2.9% to about 4% (w/w) for example 3% (w/w) of water as depicted in KF.

Crystalline form T1 of Apalutamide may be characterized by each of the above characteristics alone/or by all possible combinations, e.g., by PXRD pattern having peaks at 11.4, 18.7, 19.5, 21.1, 21.5, 26.2, 27.1 and 30.1 degrees 2-theta±0.1 degrees 2-theta and a PXRD pattern as depicted in FIG. 1.

The present disclosure comprises a crystalline form of Apalutamide designated as form T2. The crystalline form T2 of Apalutamide can be characterized by data selected from one or more of the following: a PXRD pattern having peaks at 4.5, 6.9, 13.6, 15.8, 19.8, 24.2 and 26.1 degrees 2-theta±0.1 degrees 2-theta; a PXRD pattern as depicted in FIG. 2; or combinations of these data.

Crystalline form T2 of Apalutamide may be further characterized by the PXRD pattern having peaks at 4.5, 6.9, 13.6, 15.8, 19.8, 24.2 and 26.1 degrees 2-theta±0.1 degrees 2-theta, and also having one, two, three or four additional peaks at 9.0, 10.5, 18.3 and 22.4 degrees 2-theta±0.1 degrees 2-theta; and combinations of these data.

Crystalline form T2 of Apalutamide according to any of the above embodiments, may be 2-butanol solvate.

Crystalline form T2 of Apalutamide according to any of the above embodiments may be used for the preparation of other solid state forms of Apalutamide, Apalutamide salts and solid state forms thereof. In particular, Apalutamide form T2 may be used for the preparation of Apalutamide form T11 or T13.

Without wishing to be bound by any theory, Apalutamide form T2 may be useful in purification of other solid state forms of Apalutamide, Apalutamide salts and solid state forms thereof. In particular, crystalline form T2 of Apalutamide is useful in purification of T11 or T13. Crystalline form T2 of Apalutamide may be characterized by each of the above characteristics alone/or by all possible combinations, e.g., by PXRD pattern having peaks at 4.5, 6.9, 13.6, 15.8, 19.8, 24.2 and 26.1 degrees 2-theta±0.1 degrees 2-theta and a PXRD pattern as depicted in FIG. 2.

The present disclosure comprises a crystalline form of Apalutamide designated as form T3. The crystalline form T3 of Apalutamide can be characterized by data selected from one or more of the following: a PXRD pattern having peaks at 3.6, 7.8, 10.0, 15.0, 19.3 and 25.4 degrees 2-theta±0.1 degrees 2-theta; a PXRD pattern as depicted in FIG. 3; or combinations of these data.

Crystalline form T3 of Apalutamide may be further characterized by the PXRD pattern having peaks at 3.6, 7.8, 10.0, 15.0, 19.3 and 25.4 degrees 2-theta±0.1 degrees 2-theta, and also having one or two additional peaks at 7.2 and 16.4 degrees 2-theta±0.1 degrees 2-theta; and combinations of these data.

Crystalline form T3 of Apalutamide may be characterized by each of the above characteristics alone/or by all possible combinations, e.g., by PXRD pattern having peaks at 3.6, 7.8, 10.0, 15.0, 19.3 and 25.4 degrees 2-theta±0.1 degrees 2-theta and an a PXRD pattern as depicted in FIG. 3.

Crystalline form T3 of Apalutamide according to any of the above embodiments, may be cyclohexanone solvate.

The present disclosure comprises a crystalline form of Apalutamide designated as form T4. The crystalline form T4 of Apalutamide can be characterized by data selected from one or more of the following: a PXRD pattern having peaks at 3.4, 8.2, 12.7, 13.4, 14.2, 15.8 and 19.2 degrees 2-theta±0.1 degrees 2-theta; a PXRD pattern as depicted in FIG. 4; or combinations of these data.

Crystalline form T4 of Apalutamide may be further characterized by the PXRD pattern having peaks at 3.4, 8.2, 12.7, 13.4, 14.2, 15.8 and 19.2 degrees 2-theta±0.1 degrees 2-theta, and also having one or two additional peaks at 6.8 and 13.8 degrees 2-theta±0.1 degrees 2-theta; and combinations of these data.

Crystalline form T4 of Apalutamide may be characterized by each of the above characteristics alone/or by all possible combinations, e.g., by PXRD pattern having peaks at 3.4, 8.2, 12.7, 13.4, 14.2, 15.8 and 19.2 degrees 2-theta±0.1 degrees 2-theta and a PXRD pattern as depicted in FIG. 4.

Crystalline form T4 of Apalutamide according to any of the above embodiments, may be acetonitrile-water solvate.

The present disclosure comprises a crystalline form of Apalutamide designated as form T5. The crystalline form T5 of Apalutamide can be characterized by data selected from one or more of the following: a PXRD pattern having peaks at 4.6, 9.3, 14.0, 15.0, 22.9, 23.5, 26.5 and 30.4 degrees 2-theta±0.1 degrees 2-theta; a PXRD pattern as depicted in FIG. 5; or combinations of these data.

Crystalline form T5 of Apalutamide may be further characterized by the PXRD pattern having peaks at 4.6, 9.3, 14.0, 15.0, 22.9, 23.5, 26.5 and 30.4 degrees 2-theta±0.1 degrees 2-theta, and also having one or two additional peaks at 10.7 and 18.7 degrees 2-theta±0.1 degrees 2-theta; and combinations of these data.

Crystalline form T5 of Apalutamide may be characterized by each of the above characteristics alone/or by all possible combinations, e.g., by PXRD pattern having peaks at 4.6, 9.3, 14.0, 15.0, 22.9, 23.5, 26.5 and 30.4 degrees 2-theta±0.1 degrees 2-theta and a PXRD pattern as depicted in FIG. 5.

Crystalline form T5 of Apalutamide according to any of the above embodiments may be ethylene glycol solvate.

The present disclosure comprises a crystalline form of Apalutamide designated as form T6. The crystalline form T6 of Apalutamide can be characterized by data selected from one or more of the following: a PXRD pattern having peaks at 15.9, 18.3, 19.7, 22.7, 24.0 and 24.3 degrees 2-theta±0.1 degrees 2-theta; a PXRD pattern as depicted in FIG. 6; or combinations of these data.

Crystalline form T6 of Apalutamide may be further characterized by the PXRD pattern having peaks at 15.9, 18.3, 19.7, 22.7, 24.0 and 24.3 degrees 2-theta±0.1 degrees 2-theta, and also having one, two, three or four additional peaks at 13.1, 13.9, 16.4 and 18.7 degrees 2-theta±0.1 degrees 2-theta; and combinations of these data.

Crystalline form T6 of Apalutamide according to any of the above embodiments, may be isobutanol solvate.

Crystalline form T6 of Apalutamide according to any of the above embodiments may be used for the preparation of crude Apalutamide, other solid state forms of Apalutamide, Apalutamide salts and solid state forms thereof. In particular, Apalutamide form T6 may be used for the preparation of crude Apalutamide.

Without wishing to be bound by any theory, Apalutamide form T6 may be useful in purification of crude Apalutamide, other solid state forms of Apalutamide, Apalutamide salts and solid state forms thereof. In particular, crystalline form T6 of Apalutamide is useful in purification of crude Apalutamide. Crystalline form T6 of Apalutamide may be characterized by each of the above characteristics alone/or by all possible combinations, e.g., by PXRD pattern having peaks at 15.9, 18.3, 19.7, 22.7, 24.0 and 24.3 degrees 2-theta±0.1 degrees 2-theta and a PXRD pattern as depicted in FIG. 6.

The present disclosure comprises a crystalline form of Apalutamide designated as form T7. The crystalline form T7 of Apalutamide can be characterized by data selected from one or more of the following: a PXRD pattern having peaks at 3.8, 7.7, 11.7, 13.6 and 23.1 degrees 2-theta±0.1 degrees 2-theta; a PXRD pattern as depicted in FIG. 7; or combinations of these data.

Crystalline form T7 of Apalutamide may be further characterized by the PXRD pattern having peaks at 3.8, 7.7, 11.7, 13.6 and 23.1 degrees 2-theta±0.1 degrees 2-theta, and also having one, two, three, four or five additional peaks at 14.8, 15.0, 20.3, 26.6 and 27.2 degrees 2-theta±0.1 degrees 2-theta; and combinations of these data.

Crystalline form T7 of Apalutamide may be characterized by each of the above characteristics alone/or by all possible combinations, e.g., by PXRD pattern having peaks at 3.8, 7.7, 11.7, 13.6 and 23.1 degrees 2-theta±0.1 degrees 2-theta and a PXRD pattern as depicted in FIG. 7.

Crystalline form T7 of Apalutamide according to any of the above embodiments may be methyl isobutyl ketone (MIBK) solvate.

The present disclosure comprises a crystalline form of Apalutamide designated as form T8. The crystalline form T8 of Apalutamide can be characterized by data selected from one or more of the following: a PXRD pattern having peaks at 4.1, 8.2, 16.3, 20.9 and 24.1 degrees 2-theta±0.1 degrees 2-theta; a PXRD pattern as depicted in FIG. 8; or combinations of these data.

Crystalline form T8 of Apalutamide may be further characterized by the PXRD pattern having peaks at 4.1, 8.2, 16.3, 20.9 and 24.1 degrees 2-theta±0.1 degrees 2-theta, and also having one, two, three or four additional peaks at 11.9, 17.0, 22.8 and 27.1 degrees 2-theta±0.1 degrees 2-theta; and combinations of these data.

Crystalline form T8 of Apalutamide may be characterized by each of the above characteristics alone/or by all possible combinations, e.g., by PXRD pattern having peaks at 4.1, 8.2, 16.3, 20.9 and 24.1 degrees 2-theta±0.1 degrees 2-theta and a PXRD pattern as depicted in FIG. 8.

Crystalline form T8 of Apalutamide according to any of the above embodiments may be methyl isobutyl ketone (MIBK) solvate.

The present disclosure comprises a crystalline form of Apalutamide formamide and water solvate designated as form T9. The crystalline form T9 of Apalutamide can be characterized by data selected from one or more of the following: a PXRD pattern having peaks at 4.6, 9.3, 14.0, 15.0, 23.0, 26.3 and 30.2 degrees 2-theta±0.1 degrees 2-theta; a PXRD pattern as depicted in FIG. 9; or combinations of these data.

Crystalline form T9 of Apalutamide may be further characterized by the PXRD pattern having peaks at 4.6, 9.3, 14.0, 15.0, 23.0, 26.3 and 30.2 degrees 2-theta±0.1 degrees 2-theta, and also having one or two additional peaks at 10.7 and 18.7 degrees 2-theta±0.1 degrees 2-theta; and combinations of these data.

Crystalline form T9 of Apalutamide may be characterized by each of the above characteristics alone/or by all possible combinations, e.g., by PXRD pattern having peaks at 4.6, 9.3, 14.0, 15.0, 23.0, 26.3 and 30.2 degrees 2-theta±0.1 degrees 2-theta and a PXRD pattern as depicted in FIG. 9.

Crystalline form T9 of Apalutamide according to any of the above embodiments is formamide and water solvate having about 2.19% (w/w) of formamide/water content as depicted in KF.

The present disclosure comprises a crystalline form of Apalutamide dichloromethane (DCM) and water solvate designated as form T10. The crystalline form T10 of Apalutamide can be characterized by data selected from one or more of the following: a PXRD pattern having peaks at 4.7, 9.3, 14.0, 15.0, 23.0, 26.4 and 30.4 degrees 2-theta±0.1 degrees 2-theta; a PXRD pattern as depicted in FIG. 10; or combinations of these data.

Crystalline form T10 of Apalutamide may be further characterized by the PXRD pattern having peaks at 4.7, 9.3, 14.0, 15.0, 23.0, 26.4 and 30.4 degrees 2-theta±0.1 degrees 2-theta, and also having one or two additional peaks at 10.7 and 18.7 degrees 2-theta±0.1 degrees 2-theta; and combinations of these data.

Crystalline form T10 of Apalutamide may be characterized by each of the above characteristics alone/or by all possible combinations, e.g., by PXRD pattern having peaks at 4.7, 9.3, 14.0, 15.0, 23.0, 26.4 and 30.4 degrees 2-theta±0.1 degrees 2-theta and a PXRD pattern as depicted in FIG. 10.

Crystalline form T10 of Apalutamide according to any of the above embodiments is dichloromethane and water solvate having about 1.97% (w/w) of dichloromethane/water content as depicted in KF.

The present disclosure comprises a crystalline form of Apalutamide designated as form T11. The crystalline form T11 of Apalutamide can be characterized by data selected from one or more of the following: a PXRD pattern having peaks at 15.3, 15.6, 18.9, 19.4 and 22.9 degrees 2-theta±0.1 degrees 2-theta; a PXRD pattern as depicted in FIG. 11; or combinations of these data.

Crystalline form T11 of Apalutamide may be further characterized by the PXRD pattern having peaks at 15.3, 15.6, 18.9, 19.4 and 22.9 degrees 2-theta±0.1 degrees 2-theta, and also having one, two, three, four or five additional peaks at 16.8, 24.1, 25.8, 28.2 and 28.7 degrees 2-theta±0.1 degrees 2-theta; and combinations of these data.

Crystalline form T11 of Apalutamide is a hydrate, in particular a dihydrate.

Crystalline form T11 of Apalutamide according to any of the above embodiments is a hydrate having about 6.5% to about 7.5% (w/w) for example 7% (w/w) of water as depicted in KF.

Crystalline form T11 of Apalutamide may be characterized by each of the above characteristics alone/or by all possible combinations, e.g., by PXRD pattern having peaks at 15.3, 15.6, 18.9, 19.4 and 22.9 degrees 2-theta±0.1 degrees 2-theta and a PXRD pattern as depicted in FIG. 11.

Crystalline form T11 of Apalutamide according to any of the above embodiments has higher aqueous solubility compared to other crystalline forms of Apalutamide, e.g. compared to crystalline form B of Apalutamide.

The present disclosure comprises a crystalline form of Apalutamide designated as form T12. The crystalline form T12 of Apalutamide can be characterized by data selected from one or more of the following: a PXRD pattern having peaks at 7.8, 9.8, 12.9, 17.9 and 23.2 degrees 2-theta±0.1 degrees 2-theta; a PXRD pattern as depicted in FIG. 12; or combinations of these data.

Crystalline form T12 of Apalutamide may be further characterized by the PXRD pattern having peaks at 7.8, 9.8, 12.9, 17.9 and 23.2 degrees 2-theta±0.1 degrees 2-theta, and also having one, two, three, four or five additional peaks at 15.6, 20.6, 21.1, 22.2 and 26.7 degrees 2-theta±0.1 degrees 2-theta; and combinations of these data.

Crystalline form T12 of Apalutamide may be characterized by each of the above characteristics alone/or by all possible combinations, e.g., by PXRD pattern having peaks at 7.8, 9.8, 12.9, 17.9 and 23.2 degrees 2-theta±0.1 degrees 2-theta and a PXRD pattern as depicted in FIG. 12.

Crystalline form T12 of Apalutamide may be Dimethylcarbonate solvate.

The present disclosure comprises a crystalline form of Apalutamide designated as form T13. The crystalline form T13 of Apalutamide can be characterized by data selected from one or more of the following: a PXRD pattern having peaks at 13.8, 17.1, 18.3, 22.4 and 26.8 degrees 2-theta±0.1 degrees 2-theta; a PXRD pattern as depicted in FIG. 13 alternatively a PXRD pattern as depicted in FIG. 18; or combinations of these data.

Crystalline form T13 of Apalutamide may be further characterized by the PXRD pattern having peaks at 13.8, 17.1, 18.3, 22.4 and 26.8 degrees 2-theta±0.1 degrees 2-theta, and also having one, two or three additional peaks at 13.3, 16.2 and 21.4 degrees 2-theta±0.1 degrees 2-theta; and combinations of these data.

Crystalline form T13 of Apalutamide may be a hydrate, in particular monohydrate.

Crystalline form T13 of Apalutamide according to any of the above embodiments is a hydrate having about 2.5% to about 4.5% (w/w) for example about 3% to about 4% (w/w) of water as depicted in KF. Crystalline form T13 of Apalutamide may be characterized by each of the above characteristics alone/or by all possible combinations, e.g., by PXRD pattern having peaks at 13.8, 17.1, 18.3, 22.4 and 26.8 degrees 2-theta±0.1 degrees 2-theta and a PXRD pattern as depicted in FIG. 13.

Bulk density as used in the present application is meant the ratio between mass (weight) and bulk volume for the powder blend. Tapped (tap) density is the maximum packing density of a powder (or blend of powders) achieved under the influence of well defined, externally applied forces. The minimum packed volume thus achieved depends on a number of factors including particle size distribution, true density, particle shape and cohesiveness due to surface forces including moisture. Therefore, the tap density of a material can be used to predict both its flow properties and its compressibility. These two parameters are important in the overall tableting process—which requires that loose powders be compacted into a durable solid form with the correct mechanical strength, porosity and dissolution characteristics—and in capsule filling performance. Crystalline form T13 of Apalutamide has higher bulk density and higher tap density, as compared to form A of Apalutamide which accordingly indicates better flow properties and higher compressibility.

The present disclosure comprises a crystalline form of Apalutamide designated as form T14. The crystalline form T14 of Apalutamide can be characterized by data selected from one or more of the following: a PXRD pattern having peaks at 9.7, 12.9, 15.6, 17.6, 21.8 and 23.1 degrees 2-theta±0.1 degrees 2-theta; a PXRD pattern as depicted in FIG. 14; or combinations of these data.

Crystalline form T14 of Apalutamide may be further characterized by the PXRD pattern having peaks at 9.7, 12.9, 15.6, 17.6, 21.8 and 23.1 degrees 2-theta±0.1 degrees 2-theta, and also having one, two or three additional peaks at 6.7, 23.4 and 24.0 degrees 2-theta±0.1 degrees 2-theta; and combinations of these data.

Crystalline form T14 of Apalutamide may be characterized by each of the above characteristics alone/or by all possible combinations, e.g., by PXRD pattern having peaks at 9.7, 12.9, 15.6, 17.6, 21.8 and 23.1 degrees 2-theta±0.1 degrees 2-theta and a PXRD pattern as depicted in FIG. 14.

Crystalline form T14 of Apalutamide may be an ethyl acetate solvate.

The present disclosure comprises a crystalline form of Apalutamide designated as form T15. The crystalline form T15 of Apalutamide can be characterized by data selected from one or more of the following: a PXRD pattern having peaks at 6.7, 7.8, 17.9, 23.2, 23.7 and 26.6 degrees 2-theta±0.1 degrees 2-theta; a PXRD pattern as depicted in FIG. 15; or combinations of these data.

Crystalline form T15 of Apalutamide may be further characterized by the PXRD pattern having peaks at 6.7, 7.8, 17.9, 23.2, 23.7 and 26.6 degrees 2-theta±0.1 degrees 2-theta, and also having one, two, three or four additional peaks at 13.0, 18.3, 21.1 and 21.5 degrees 2-theta±0.1 degrees 2-theta; and combinations of these data.

Crystalline form T15 of Apalutamide may be characterized by each of the above characteristics alone/or by all possible combinations, e.g., by PXRD pattern having peaks at 6.7, 7.8, 17.9, 23.2, 23.7 and 26.6 degrees 2-theta±0.1 degrees 2-theta and a PXRD pattern as depicted in FIG. 15.

Crystalline form T15 of Apalutamide may be a methyl acetate solvate.

The present disclosure comprises a crystalline form of Apalutamide designated as form T16. The crystalline form T16 of Apalutamide can be characterized by data selected from one or more of the following: a PXRD pattern having peaks at 12.2, 17.8, 21.8, 25.1 and 26.2 degrees 2-theta±0.1 degrees 2-theta; a PXRD pattern as depicted in FIG. 16; or combinations of these data.

Crystalline form T16 of Apalutamide may be further characterized by the PXRD pattern having peaks at 12.2, 17.8, 21.8, 25.1 and 26.2 degrees 2-theta±0.1 degrees 2-theta, and also having one, two or three additional peaks at 9.6, 15.7 and 23.2 degrees 2-theta±0.1 degrees 2-theta; and combinations of these data.

Crystalline form T16 of Apalutamide may be characterized by each of the above characteristics alone/or by all possible combinations, e.g., by PXRD pattern having peaks at 12.2, 17.8, 21.8, 25.1 and 26.2 degrees 2-theta±0.1 degrees 2-theta and a PXRD pattern as depicted in FIG. 16.

Crystalline form T16 of Apalutamide may be a methyl ethyl ketone solvate.

The present disclosure comprises a crystalline form of Apalutamide designated as form T17. The crystalline form T17 of Apalutamide can be characterized by data selected from one or more of the following: a PXRD pattern having peaks at 7.7, 12.3, 15.0, 18.1 and 20.8 degrees 2-theta±0.1 degrees 2-theta; a PXRD pattern as depicted in FIG. 17; or combinations of these data.

Crystalline form T17 of Apalutamide may be further characterized by the PXRD pattern having peaks at 7.7, 12.3, 15.0, 18.1 and 20.8 degrees 2-theta±0.1 degrees 2-theta, and also having one, two, three, four or five additional peaks at 10.4, 15.5, 16.7, 19.3 and 19.9 degrees 2-theta±0.1 degrees 2-theta; and combinations of these data.

Crystalline form T17 of Apalutamide may be characterized by each of the above characteristics alone/or by all possible combinations, e.g., by PXRD pattern having peaks at 7.7, 12.3, 15.0, 18.1 and 20.8 degrees 2-theta±0.1 degrees 2-theta and a PXRD pattern as depicted in FIG. 17.

Crystalline form T17 of Apalutamide may be an acetonitrile solvate.

The present disclosure also provides the use of the solid state forms of Apalutamide and salts thereof, for preparing other solid state forms of Apalutamide, Apalutamide salts and solid state forms thereof.

The present disclosure further encompasses processes for preparing Apalutamide salts or solid state forms thereof. The process comprises preparing the solid state form of the present disclosure, and converting it to Apalutamide salt. The conversion can be done, for example, by a process comprising reacting the obtained Apalutamide with an appropriate acid to obtain the corresponding acid addition salt.

In another embodiment the present disclosure encompasses the above described solid state forms of Apalutamide and salts thereof, for use in the preparation of other solid state forms of Apalutamide and salts thereof.

In another embodiment the present disclosure encompasses the above described solid state forms of Apalutamide and salts thereof, or combinations thereof, for use in the preparation of pharmaceutical compositions and/or formulations, preferably for the treatment of cancer, in particular prostate cancer.

In another embodiment the present disclosure encompasses the use of the above described solid state forms of Apalutamide and salts thereof, or combinations thereof, for the preparation of pharmaceutical compositions and/or formulations, preferably oral formulations, e.g. tablet or capsule.

The present disclosure further provides pharmaceutical compositions comprising the solid state forms of Apalutamide and salts thereof, or combinations thereof, according to the present disclosure.

In yet another embodiment, the present disclosure encompasses pharmaceutical formulations comprising at least one of the above described solid state forms of Apalutamide and salts thereof, and at least one pharmaceutically acceptable excipient.

The present disclosure encompasses a process to prepare said formulations of Apalutamide comprising combining at least one of the above solid state forms and at least one pharmaceutically acceptable excipient.

The solid state forms as defined herein, as well as the pharmaceutical compositions or formulations of Apalutamide can be used as medicaments, particularly for the treatment of cancer, in particular prostate cancer.

The present disclosure also provides a method of treating cancer, in particular prostate cancer, comprising administering a therapeutically effective amount of any one or combination of the solid state forms of Apalutamide of the present disclosure, or at least one of the above pharmaceutical compositions or formulations, to a subject suffering from cancer, in particular prostate cancer or otherwise in need of the treatment.

The present disclosure also provides the use of any one or combination of the solid state forms of Apalutamide of the present disclosure, or at least one of the above pharmaceutical compositions or formulations for the manufacture of a medicament for cancer, in particular prostate cancer.

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Analytical Methods

Powder X-Ray Diffraction Pattern ("PXRD") Method for T1, T2, T5, T6, T7, T8, T9, T10, T11 and T13

X-ray diffraction was performed on X-Ray powder diffractometer:

Bruker D8 Advance; CuK_radiation ($\lambda$=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement parameters:
Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.

Powder X-Ray Diffraction (XRD) Method for T3, T4, T12, T14, T15, T16 and T17

X-ray diffraction was performed on X-Ray powder diffractometer:

X'Pert PRO PANalytical; CuK_radiation ($\lambda$=1.5418 Å); PIXcel detector; laboratory temperature 22-25° C.; The samples were gently ground by means of mortar and pestle in order to obtain a fine powder.

Measurement parameters:
Scan range (°): 3.000-40.001
Step size (°): 0.0131303
Time per Step (s): 20.4
No. of steps: 2818
Scan mode: Continuous
Sample spinning (Rotation time (s): Without Spin Karl Fischer Method Water content analysis was performed on Metrohm 890 Titando instrument. About 100 mg sample was added to the titrator, the water content is measured in % w/w by measuring the amount of iodine consumed as a result of reaction with water in the sample.

Solid State NMR

Solid-state 13C NMR spectra were recorded with variable amplitude cross polarization, magic angle spinning and high power proton decoupling using a BRUKER Avance III+ spectrometer operating at 400 MHZ at room temperature. A probe using 4 mm o.d. zirconia rotors was employed. The operation conditions were: contact time: 3 ms; recycle delay: 2 s; 5100 scans and spin rate of 11 KHz. Chemical shifts were referenced via a replacement sample of glycine (carboxyl carbon chemical shift assigned as 176.03 ppm relative to the signal of tetramethylsilane).

Solubility Study

Solubility of Apalutamide was checked using Dissolution apparatus (Lab India D8000) at 37 deg.

Buffers pH. 1.2, 4.5 and 6.8 were prepared as per the USP 36 Solutions/Buffer Solutions 1209.

About 500 mg of Apalutamide were added to the 100 mL buffer (pH 1.2, 4.5 and 6.8) in individual flasks to obtain saturated suspension and the suspension was stirred with 250 rpm for 24 hours. Suspension was observed though out stirring period. Samples were drawn at different intervals on completion of 15 mins, 1 hrs, 4 hrs and 24 hrs from each flask and filtered through 0.45μ PTFE filter; each solution was analyzed for Apalutamide content by liquid chromatography.

Method of analysis of Liquid chromatography:

| Agilent Zorbax RX C8, 250 * 4.6 mm, | Gradient | | |
|---|---|---|---|
| 5 micron (or equivalent) | TIME | A | B |
| Buffer: 0.5% HClO$_4$ in water | 0 | 50 | 50 |
|  | 5 | 50 | 50 |
| Mobile phase A: BUFFER | 10 | 40 | 60 |
| Mobile phase B: Acetonitrile | 15 | 20 | 80 |
| Flow: 1.0 ml/min | 16 | 50 | 50 |
| UV: 242 nm |  |  |  |
| Diluent: ACN + WATER (50 + 50) | 21 | 50 | 50 |
| Standard Preparation: 0.1 mg/mL of diluent |  |  |  |
| Sample Preparation: inject direct sample solution obtained from the solubility study |  |  |  |
| Column Temperature: 25° C. |  |  |  |
| Sampler Temperature: 10° C. |  |  |  |

EXAMPLES

The starting material Apalutamide may be obtained according to reference example 1.

Reference Example 1

Stage-1: Process for the Preparation of 2-Fluoro-N-methyl-4-nitrobenzamide

Charge 100 g of 2-Fluoro-4-nitrobenzoic acid, 300 ml of toluene and 1.0 ml DMF at 20-35° C. and stir mixture for 5 min. To this, slowly charge 96 g Thionyl chloride at 20-35° C. and stir for 5 min. Heat the reaction mixture to 60-65° C. and stir for 3 h and monitored reaction by HPLC for unreacted 2-Fluoro-4-nitrobenzoic acid. Cool the reaction mixture to 20-35° C. and add this solution slowly in to another flask containing pre-cooled 40% aq. methyl amine (250 mL). After addition, stir the slurry for 1 h at 25-35° C. and charge 700 ml of water, stir the slurry for 1 h at 30-35° C. Filter the slurry and wash the wet cake twice with 100 ml of water. Dry the solid and dry wt is 100 g (Yield. 93.45%).

Stage-2: Process for the Preparation of 4-Amino-2-fluoro-N-methylbenzamide

Charge 100 g of 2-Fluoro-N-methyl-4-nitrobenzamide and 500 ml of methanol into the 1 L autoclave at ambient temperature. To this add, 35 ml of Encapsulated Raney Ni (previously washed with water) and 3 g of acetic acid. Close the autoclave and flush with nitrogen for 2 times and then pressurized with hydrogen to 5.0 Kg and maintain until completion of the reaction. After completion of the reaction filter the catalyst and wash with 50 ml of methanol. Concentrate the filtrate to remove the methanol under vacuum at 45-50° C. to a thick residue and add 300 ml of water, stir slurry for 1 h and filter, wash with 50 ml of water. Dry the product and dry wt is 70 g (83.3%).

Stage-3: Process for the Preparation of 4-(1-Cyano-cyclobutylamino)-2-fluoro-N-methylbenzamide Charge 100 g of 4-Amino-2-fluoro-N-methylbenzamide, 44 g of sodium cyanide, 300 ml of Methanol and 62 g of cyclobutanone and stir for 5 min. To this, add slowly 100 ml acetic acid while maintain temperature 25-40° C. and stir the reaction mixture for 10-15 min. Heat the reaction mixture to 60-70° C. and maintain for 10-12 h. Cool the reaction mixture to 20-30° C. and adjust the pH to about 7.5-8.0 by using aqueous 3% NaOH solution at 25-35° C. and stir for 1-2 h. Filter the slurry and wash the wet cake twice with 100 ml of water. Purify the crude material using 500 ml of isopropanol (IPA) at reflux condition for 30 min and cool to ambient temperature and filter the solid, wash with 100 ml isopropanol. Dry the solid and dry wt is 125 g (85%).

Stage-4: Process for the Preparation of 4-[7-[6-cyano-5-(trifluoromethyl)pyridin-3-yl]-8-oxo-6-thioxo-5,7-diazaspiro[3.4]octan-5-yl]-2-fluoro-N-methylbenzamide Charged 60.0 gm of 4-[(1-Cyano cyclobutyl)amino]-2-fluoro-N-methylbenzamide, Dimethylacetamide and 69.5 gm of 5-Amino-3-(trifluoromethyl)-2-pyridinecarbonitrile at below 35° C. under $N_2$ atmosphere. The obtained slurry was cooled to 0-5° C. then 42.7 g of thiophosgene was added slowly to the slurry at 0-5° C. and maintained for 5-10 min at same temperature (0-5° C.), gently raise the reaction mass temperature to room temperature then heat the reaction mixture to 60-65° C. and maintained for 5 hr (to ensure the unreacted $1^{st}$ component should be <20.0% by HPLC), once its complies then cooled the reaction mixture to below 25° C., then charged 900 ml of methanol and 6.0 gm of Norit charcoal, stirred for 30 min at 20-30° C. The obtained reaction mass was filtered through hyflo then 480 ml (2M) Hydrochloride was charged to the filtrate at 20-30° C., heated the reaction mass to 60-65° C. and maintained for 2 hr, then cooled to 20-25° C. Slowly quenched the reaction mass to the 1500 ml prechilled (0-5° C.) DM Water and maintained for 30-45 min at same temperature. The slurry was filtered and washed with prechilled DM Water kept the solid under vacuum suction for 1 hr to obtain the crude. Dissolved the crude in 600 ml of IPA and heat the slurry to reflux in order to obtained the clear solution and maintain for 30 min then slowly cool the solution to 0-5° C. and slurry was stirred for 1 hr at 0-5° C. The obtained slurry was filtered and washed with 60 ml of chilled IPA and kept for vacuum suction for 1 hr to obtain 90 gm of wet material.

Example 1: Preparation of Apalutamide Form T1

Apalutamide (IPA Wet cake; IPA content about 5.6% w/w) 90 gm was dissolved in 300 ml of methanol at reflux temperature (60-65° C.) and the obtained clear solution was maintained for 30-45 min. Then the solution was cooled to 0-5° C. for a period of 115 mins, and stirred for 1 hr. The obtained slurry was filtered under vacuum then washed with 0.5V of methanol and kept under suction for 60 min. The compound was dried at 50-60° C. for 12 hr under vacuum to obtain Form T1 wt. 70 gm. Apalutamide form T1 has been confirmed by PXRD as presented in FIG. 1.

Example 2: Preparation of Apalutamide Form T2

Apalutamide (Form T1) 0.25 gm was added in 5 ml of 2-Butanol at 20-25° C. and the obtained slurry were stirred for 3 Days. The obtained solid was filtered under vacuum and kept under suction for about 10 minutes to obtain apalutamide form T2 0.17 gm. Apalutamide form T2 has been confirmed by PXRD as presented in FIG. 2.

Example 3: Preparation of Apalutamide form T3

Apalutamide (Form T1) 0.3 gm was dissolved in 1.5 ml of cyclohexanone at 80° C. and maintained the clear solution at 80° C. for 15 min then cooled the solution to 25° C. Distilled off the solvent under vacuum (less than 10 mbar) at 25° C. The obtained solid was dried at RT (25° C.) for 1 hr to obtain apalutamide Form T3 0.3 gm. Apalutamide form T3 has been confirmed by PXRD as presented in FIG. 3.

Example 4: Preparation of Apalutamide Form T4

Apalutamide (Form T1) 0.3 gm was dissolved in 1.5 ml of Acetonitrile at 65° C. and maintained the clear solution at 65° C. for 15 min then cooled the solution to 25°. Distilled off the solvent under vacuum (less than 10 mbar) at 25° C. The obtained solid was dried at RT (25° C.) for 1 hr to obtain apalutamide Form T4 0.3 gm. Apalutamide form T4 has been confirmed by PXRD as presented in FIG. 4.

Example 5: Preparation of Apalutamide Form T5

Apalutamide (Form T1) 0.25 gm was added in 5 ml of ethylene glycol at 20-25° C. and the obtained slurry was stirred for 24 hrs. The obtained solid was filtered under vacuum and kept under suction for about 10 minutes to obtain apalutamide Form T5 0.15 gm. Apalutamide form T5 has been confirmed by PXRD as presented in FIG. 5.

Example 6: Preparation of Apalutamide Form T6

Apalutamide (Form T1) 0.25 gm was added in 5 ml of isobutanol at 20-25° C. and the obtained slurry was stirred for 24 hrs. The obtained solid was filtered under vacuum and kept under suction for about 10 minutes to obtain apalutamide Form T6 0.17 gm. Apalutamide form T6 has been confirmed by PXRD as presented in FIG. 6.

Example 7: Preparation of Apalutamide Form T7

Apalutamide (Form T1) 0.5 gm was added in 1 ml of MIBK (Methyl isobutyl ketone) at 20-25° C. and the obtained slurry was stirred for 15 min. The obtained solid was filtered under vacuum and kept under suction for about 10 minutes at 20-25° C. to obtain apalutamide Form T7 0.4 gm. Apalutamide form T7 has been confirmed by PXRD as presented in FIG. 7.

Example 8: Preparation of Apalutamide Form T8

Apalutamide (Form T1) 0.2 gm was added in 0.6 ml of MIBK (Methyl isobutyl ketone) at 20-25° C. and the obtained slurry was stirred for 3 days at 20-25° C. The obtained solid was filtered under vacuum and kept under suction for about 20 minutes at 20-25° C. to obtain Apalutamide Form T8 0.14 gm. Apalutamide form T8 has been confirmed by PXRD as presented in FIG. 8.

Example 9: Preparation of Apalutamide Form T8

Apalutamide (Form T1) 0.3 gm was dissolved in 5 ml of MIBK (Methyl isobutyl ketone) at 70° C. and maintained the clear solution at 70° C. for 15 min then immediately cooled the solution to 0-5° C. Distilled off the solvent under vacuum (less than 10 mbar) at 0-5° C. The obtained solid was dried at 0-5° C. for 2 hr to obtain Apalutamide Form T8 (0.3 gm) as confirmed by PXRD.

Example 10: Preparation of Apalutamide Form T9

Apalutamide (Form T1) 0.25 gm was added in 5 ml of Formamide at 20-25° C. and the obtained slurry was stirred for 24 hr at 20-25° C. The obtained solid was filtered under vacuum and kept under suction for about 30 minutes at 20-25° C. to obtain Apalutamide Form T9 0.17 gm. Apalutamide form T9 has been confirmed by PXRD as presented in FIG. 9.

Example 11: Preparation of Apalutamide Form T9

Apalutamide (Form T1) 0.25 gm was added in 5 ml of Formamide at 20-25° C. and the obtained slurry was stirred for 7 Days at 20-25° C. The obtained solid was filtered under vacuum and kept under suction for about 30 minutes at 20-25° C. to obtain Apalutamide Form T9 (0.16 gm) as confirmed by PXRD.

Example 12: Preparation of Apalutamide Form T9

Apalutamide (Form T1) 0.25 gm was added in 5 ml of Formamide at 20-25° C. and the obtained slurry was stirred for 3 Days at 20-25° C. The obtained solid was filtered under vacuum and kept under suction for about 30 minutes at 20-25° C. to obtain Apalutamide Form T9 (0.16 gm) as confirmed by PXRD.

Example 13: Preparation of Apalutamide Form T9

Apalutamide (Form T1) 0.2 gm was added in 5 ml of Formamide at 60° C. and the obtained slurry was stirred for 7 Days at 60° C. The obtained solid was filtered under vacuum and kept under suction for about 30 minutes at 20-25° C. to obtain Apalutamide Form T9 (0.16 gm) as confirmed by PXRD.

Example 14: Preparation of Apalutamide Form T10

Apalutamide (Form T1) 0.2 gm was added in 0.5 ml of DCM (Dichloromethane) at 20-25° C. and the obtained slurry was stirred for 3 days at 20-25° C. The obtained solid was filtered under vacuum and kept under suction for about 10 minutes at 20-25° C. to obtain Apalutamide Form T10 0.15 gm. Apalutamide form T10 has been confirmed by PXRD as presented in FIG. 10.

Example 15: Preparation of Apalutamide Form T10

Apalutamide (Form T1) 0.3 gm was dissolved in 1.5 ml of DCM (Dichloromethane) at 30° C. and maintained the clear solution at 30° C. for 15 min. Distilled off the solvent under vacuum (600 Torr) at 30° C. The obtained solid was dried at 30° C. for 1 hr to obtain Apalutamide Form T10 (0.2 gm) as confirmed by PXRD.

Example 16: Preparation of Apalutamide Form T11

Apalutamide (Form T4) 0.5 gm was kept exposed for 2 days at 20-25° C. and 80% RH to obtained apalutamide Form T11. Apalutamide form T11 has been confirmed by PXRD as presented in FIG. 11.

Example 17: Preparation of Apalutamide Form T12

Apalutamide (Form T1) 0.3 gm was dissolved in 5 ml of DMC (Dimethyl carbonate) at 60° C. and maintained the clear solution at 60° C. for 15 min then cooled the solution to 0-5° C. Distilled off the solvent under vacuum (less than 10 mbar) at 0-5° C. The obtained solid was dried at 0-5° C. for 2 hr to obtain Apalutamide Form T12 0.1 gm. Apalutamide form T12 has been confirmed by PXRD as presented in FIG. 12.

Example 18: Preparation of Apalutamide Form T12

Apalutamide (Form T1) 0.3 gm was dissolved in 5 ml of DMC (Dimethyl carbonate) at 60° C. and maintained the clear solution at 60° C. for 15 min then cooled the solution to 25-30° C. Distilled off the solvent under vacuum (less than 10 mbar) at 25-30° C. The obtained solid was dried at 25-30° C. for 1 hr to obtain Apalutamide Form T12 (0.3 gm) as confirmed by PXRD.

Example 19: Preparation of Apalutamide Form T13

Apalutamide (Form T1) 10.0 gm and 70 ml of Dichloromethane was added in flask, stirred for 10 min at 40° C. to obtain a clear solution and distilled off the solvent under vacuum (less than 10 mbar) at 40° C. in 15 min. The obtained solid was dried at 50° C. for 3 hr under vacuum to obtain amorphous Apalutamide 9.0 gm.
Tg: Onset temperature: 98° C.
Apalutamide (amorphous form) 0.15 gm was suspended in 3 ml of DM Water and was left at variable temperature as follows: heating from 20° C. to 35° C. at 20° C./min., held at 35° C. for 30 min, cooling from 35° C. to 25° C. at 20° C./min., held at 25° C. for 60 min., heated from 25° C. to 35° C. at 10° C./min., held at 35° C. for 30 min., cooling from 35° C. to 10° C. at 10° C./min., held at 10° C. for 60 min. The obtained solid was filtered under vacuum and kept under suction for about 30 minutes at 20-25° C. to obtain apalutamide Form T13 0.10 gm. Apalutamide form T13 has been confirmed by PXRD as presented in FIG. 13.

Example 20: Preparation of Apalutamide Form T14

Apalutamide (Form T1) 3.0 gm was added in 6.0 ml Ethyl acetate at 25-30° C. and stirred at 25-30° C. for 24 hrs. The obtained solid was filtered and a saturated solution was collected. 0.6 ml of above saturated solution was taken in a test tube at 25-30° C. and 3 ml of Methyl cyclohexane was added under stirring. The solid crystallized out after 1 hr and the reaction mass was stirred for 30 min at 25-30° C. The obtained solid was filtered under vacuum and kept under suction for about 30 minutes at 25-30° C. to obtain apalutamide Form T14 0.10 gm. Apalutamide form T14 has been confirmed by PXRD as presented in FIG. 14.

Example 21: Preparation of Apalutamide Form T14

Apalutamide (Form T1) 3.0 gm was added in 6.0 ml Ethyl acetate at 25-30° C. and stirred at 25-30° C. for 24 hrs. The obtained solid was filtered and a saturated solution was collected. 0.6 ml of above saturated solution was taken in a test tube at 25-30° C. and 3 ml of any one of the solvent consisting of (a) n-Heptane; (b) ethyl acetate; and (c) methyl tert-butyl ether was added under stirring. The solid crystallized out after 1 hr and the reaction mass was stirred for 30 min at 25-30° C. The obtained solid was filtered under vacuum and kept under suction for about 30 minutes at 25-30° C. to obtain apalutamide Form T14 0.10 gm as confirmed by PXRD.

Example 22: Preparation of Apalutamide Form T15

Apalutamide (Form T1) 0.3 gm was dissolved in 5 ml of methyl acetate at 60° C. and maintained a clear solution at 60° C. for 15 min. The solution was cooled to 25° C. for 20 min and the solvent was distilled off under vacuum (600 mbar) at 25° C. for 11 hr to obtain apalutamide Form T15 0.2 gm. Apalutamide form T15 has been confirmed by PXRD as presented in FIG. 15.

Example 23: Preparation of Apalutamide Form T15

Apalutamide (Form T1) 3.0 gm was added in 6.0 ml Methyl acetate at 25-30° C. and stirred at 25-30° C. for 24 hrs. The obtained solid was filtered and a saturated solution was collected. 0.6 ml of above saturated solution was taken in a test tube at 25-30° C. and 3 ml of any one of the solvent consisting of: (a) cyclohexane; (b) methyl acetate; (c) n-heptane was added under stirring. The solid crystallized out after 30 min and the reaction mass was stirred for 30 min at 25-30° C. The obtained solid was filtered under vacuum and kept under suction for about 30 minutes at 25-30° C. to obtain Apalutamide form T15 0.10 gm.

Example 24: Preparation of Apalutamide Form T16

Apalutamide (Form T1) 0.3 gm was dissolved in 5 ml of methyl ethyl ketone at 60° C. and maintained a clear solution at 60° C. for 15 min. The solution was cooled to 25° C. for 30 min. The solvent was distilled off under vacuum (600 mbar) at 25° C. for 12 hr to obtain apalutamide form T16 0.2 gm. Apalutamide form T16 has been confirmed by PXRD as presented in FIG. 16.

Example 25: Preparation of Apalutamide Form T17

Apalutamide (Form T2) 10 gm was dissolved in 80 ml of Acetonitrile at 35° C. and maintained the clear solution at 35° C. for 10 min then filtered the clear solution under vacuum and transfer the clear solution into another RBF, added 320 ml prechilled water (0-5° C.) within 10 min to the clear solution then maintained the slurry for 1 hr at 27-30° C. The obtained solid was filtered under vacuum and air dried at RT (25-30° C.) for 2 hr to obtain apalutamide Form T17 wt. 7 gm. Apalutamide form T17 has been confirmed by PXRD as presented in FIG. 17.

Example 26: Preparation of Apalutamide Form T17

Apalutamide (Form T1, prepared according to example 1) 1 gm was added in 5 ml of acetonitrile at 20-25° C. and the obtained slurry were stirred for 30 min. The obtained solid was filtered under vacuum and kept under suction for about 10 minutes and dried under vacuum at 30° C. for 2 hr to obtain apalutamide T17 wt. 0.8 gm.

Example 27: Preparation of Apalutamide Form T13

375 ml of water and 1.25 g (5%) T13 seed were added at 20-25° C. into a reactor. In another flask 25 gm of Apalutamide (form T17) wet (LOD: 40-60%) was dissolved in 100 ml of acetone at 25-30° C. and maintained a clear solution for 5 min at 20-30° C. The clear solution was filtered under vacuum at 25-30° C. (particle free filtration). The clear solution (filtrate) was added into the reactor within 5-10 min and the reaction mass was stirred for 2 hr at 20-30° C. The obtained solid was filtered under vacuum and kept for suction for 30 min then dried the solid under vacuum at 60° C. for 6 hr to obtained apalutamide form T13 wt: 22.5 gm.

Example 28: Preparation of Apalutamide Form T13

20 g Apalutamide form T11 wet (LOD: 40-60%) was slurred in 120 ml of water at 20-30° C. and the obtained slurry was stirred for 6-8 hr at same temperature. The obtained solid was filtered under vacuum and kept for vacuum suction for about 30 min to obtain 19.5 g of Apalutamide T13 Wet which was further dried in Air for 40-50 h at 20-30° C. to obtain Apalutamide form T13.

Example 29: Preparation of Apalutamide Form T13 Via T2 and T11

Step A: Main Reaction 100 gm of 4-[(1-Cyano cyclobutyl)amino]-2-fluoro-N-methylbenzamide, Dimethylacetamide 650 ml and 90.9 gm of 5-Amino-3-(trifluoromethyl)-2-pyridinecarbonitrile were charged at below 35° C. under $N_2$ atmosphere. The obtained slurry was cooled to −5 to 5° C. then 70 g of thiophosgene was added slowly to the slurry at −5 to 5° C. and maintained for 5-10 min at same temperature (0-5° C.), gently raise the reaction mass temperature to room temperature then heat the reaction mixture to 60-65° C. and maintained for 5 hr (to ensure the unreacted 1st component should be <20.0% by HPLC, once its complies then cooled the reaction mixture to below 25° C. (reaction mass wt: 854 g).

Step B: Crude Isolation 213.5 g from the reaction mass obtained in step A was taken, 200 ml of 2-butanol and 50 ml (2M) Hydrochloride was charged, the reaction mass was heated to 60-65° C. and maintained for 2 hr, then cooled to 25-35° C. to obtain a solution. 200 ml water were slowly added into the clear solution and maintained for 60-90 min at same temperature to obtain a slurry. The slurry was cooled further to 0-5° C. and maintained for 60 min. The slurry was filtered and washed with 12.5 ml of prechilled 2-butanol, kept the solid under vacuum suction for 30 min to obtain 37.5 g of crude wet.

Step C: Preparation of Form T2

18.7 g wet crude obtained in step B was dispersed in 62.5 ml of 2-Butanol to obtain a slurry. The slurry was heated to 70-80° C. in order to obtain a clear solution. 0.62 g Norit CGP charcoal was added and maintain for 30 min. Reaction mass was filtered through hyflo then washed with 18.7 ml of hot 2-butanol (hyflow filtration at 70-80° C.) to obtain a clear solution. The clear solution was charged into another round bottom flask then the solution was slowly cooled to 20-30° C. and slurry was stirred for 2 hr at 20-30° C. The obtained slurry was filtered and washed with 12.5 ml of 2-Butanol and kept for vacuum suction for 30 min to obtain 16 gm of form T2 wet material.

Step D: Preparation of Form T11

15 g Apalutamide wet (2-Butanol) obtained in step C was dissolved in 60 ml of Acetonitrile and stirred for 10 min at RT (25-30° C.) in order to get the clear solution and filtered through 0.2 micron filter. The clear solution was charged into another round bottom flask, 90 ml of prechilled water (8-10° C.) were added over the period of 5-10 min. The reaction mass was gradually cooled to 0-5° C. and maintain for 2 hrs at 0-5° C. The obtained solid was filtered under vacuum and kept for vacuum suction for 30 min. to obtain 22 gm of wet material (form T11 wet).

Step E: Preparation of Form T13

20 g Apalutamide wet obtained in step D was slurred in 120 ml of water at 20-30° C. and the obtained slurry was stirred for 6-8 hr at same temperature. The obtained solid was filtered under vacuum and kept for vacuum suction for about 30 min to obtain 19.5 g of Apalutamide form T13 Wet which was dried in Air dryer for 40-50 h at 20-30° C.

Example 30: Preparation of Apalutamide form T13 from Crude Purification from Methanol Via T2 and T11

Step A 140 gm of 4-[(1-Cyano cyclobutyl)amino]-2-fluoro-N-methylbenzamide, Dimethylacetamide 910 ml and 127 gm of 5-Amino-3-(trifluoromethyl)-2-pyridinecarbonitrile were charged at below 35° C. under $N_2$ atmosphere. The obtained slurry was cooled to −5 to 5° C. then 97.6 g of thiophosgene was added slowly to the slurry at −5 to 5° C. and maintained for 5-10 min at same temperature (0-5° C.), the reaction mass temperature was gently raised to room temperature then the reaction mixture was heated to 60-65° C. and maintained for 7 hr (to ensure the unreacted 1st component should be <20.0% by HPLC), once its complies then the reaction mixture was cooled to below 25° C., then 420 ml of methanol and 280 ml (2M) Hydrochloride were charged, the reaction mass was heated to 60-65° C. and maintained for 2 hr, then cooled to 20-25° C. The reaction mass was slowly quenched to a 1120 ml purified water at RT and maintained for 60 min at same temperature, then chilled to 0-5° C. and maintain for 60 min. The slurry was filtered and washed with 280 ml of prechilled purified water. The solid was kept under vacuum suction for 30 min to obtain 360 g of crude.

Step B 257 g of the crude was dissolved in 600 ml of 2-Butanol, heated to 70-80° C. and maintained for 30 min then the solution was slowly cooled to 20-30° C. and slurry was stirred for 2 hr at 20-30° C. The obtained slurry was filtered and washed with 100 ml of 2-Butanol and kept for vacuum suction for 30 min to obtain 150 gm of wet material.

Step C 140 g Apalutamide wet (2-Butanol) obtained in step B was dissolved in 420 ml of Acetonitrile and stirred for 30 min at RT (25-30° C.) in order to get the clear solution and 14 g of Norit CGP Charcoal was charged, stirred for 30 min. The obtained reaction mass was filtered through hyflo then washed with 140 ml of Acetonitrile. The clear solution was charged into another round bottom flask, 840 ml of pre-chilled water (8-10° C.) were added over the period of 5-10 min and the reaction mass was gradually cooled to 0-5° C. and maintain for 2 hrs at 0-5° C. The obtained solid was filtered under vacuum and kept for vacuum suction for 30 min to obtain 180 gm of wet material (T11).

Step D 175 g Apalutamide wet obtained in step C was slurred in 1050 ml of water at 20-30° C. and the obtained slurry was stirred for 6-8 hr at same temperature. The obtained solid was filtered under vacuum and wet cake was washed with 175 ml purified water and kept for vacuum suction for about 30 min to obtain 215 g of Apalutamide T13 Wet. The compound was dried in Air dryer for 40-50 h at 20-30° C., dry wt. 77.5 g.

The invention claimed is:

1. A solid state form of Apalutamide selected from:
   (A) crystalline form T13, which is characterized by data selected from one or more of the following:
      (i) a PXRD pattern having peaks at 13.8, 17.1, 18.3, 22.4 and 26.8 degrees 2-theta±0.1 degrees 2-theta;
      (ii) a PXRD pattern as depicted in FIG. 13, alternatively a PXRD pattern as depicted in FIG. 18;
      (iii) a PXRD pattern having peaks at 13.8, 17.1, 18.3, 22.4 and 26.8 degrees 2-theta±0.1 degrees 2-theta, and also having one, two or three additional peaks at 13.3, 16.2 and 21.4 degrees 2-theta±0.1 degrees 2-theta;
   or
   (B) crystalline form T11, which is characterized by data selected from one or more of the following:
      (i) a PXRD pattern having peaks at 15.3, 15.6, 18.9, 19.4, 22.9, and 28.7 degrees 2-theta±0.1 degrees 2-theta;
      (ii) a PXRD pattern as depicted in FIG. 11;
      (iii) a PXRD pattern having peaks at 15.3, 15.6, 18.9, 19.4, 22.9, and 28.7 degrees 2-theta±0.1 degrees 2-theta, and also having one, two, three, or four additional peaks at 16.8, 24.1, 25.8, and 28.2 degrees 2-theta±0.1 degrees 2-theta.

2. A solid state form of Apalutamide crystalline form T2, which is characterized by data selected from one or more of the following:
   (i) a PXRD pattern having peaks at 4.5, 6.9, 13.6, 15.8, 19.8, 24.2 and 26.1 degrees 2-theta±0.1 degrees 2-theta;
   (ii) a PXRD pattern as depicted in FIG. 2;
   (iii) a PXRD pattern having peaks at 4.5, 6.9, 13.6, 15.8, 19.8, 24.2 and 26.1 degrees 2-theta±0.1 degrees 2-theta, and also having one, two, three or four additional peaks at 9.0, 10.5, 18.3 and 22.4 degrees 2-theta±0.1 degrees 2-theta.

3. Crystalline form T13 of Apalutamide according to claim 1, which is characterized by data selected from one or more of the following:
   (i) a PXRD pattern having peaks at 13.8, 17.1, 18.3, 22.4 and 26.8 degrees 2-theta±0.1 degrees 2-theta;
   (ii) a PXRD pattern as depicted in FIG. 13, alternatively a PXRD pattern as depicted in FIG. 18;
   (iii) a PXRD pattern having peaks at 13.8, 17.1, 18.3, 22.4 and 26.8 degrees 2-theta±0.1 degrees 2-theta, and also having one, two or three additional peaks at 13.3, 16.2 and 21.4 degrees 2-theta±0.1 degrees 2-theta.

4. Crystalline form T11 of Apalutamide according to claim 1, which is characterized by data selected from one or more of the following:
   (i) a PXRD pattern having peaks at 15.3, 15.6, 18.9, 19.4, 22.9, and 28.7 degrees 2-theta±0.1 degrees 2-theta;
   (ii) a PXRD pattern as depicted in FIG. 11;
   (iii) a PXRD pattern having peaks at 15.3, 15.6, 18.9, 19.4, 22.9, and 28.7 degrees 2-theta±0.1 degrees 2-theta, and also having one, two, three, or four additional peaks at 16.8, 24.1, 25.8, and 28.2 degrees 2-theta±0.1 degrees 2-theta.

5. Crystalline form T2 of Apalutamide according to claim 2, which is characterized by a PXRD pattern having peaks at 4.5, 6.9, 13.6, 15.8, 19.8, 24.2 and 26.1 degrees 2-theta±0.1 degrees 2-theta.

6. The solid state form of Apalutamide according to claim 3, wherein crystalline form T13 is a monohydrate.

7. The solid state form of Apalutamide according to claim 4, wherein crystalline form T11 is a dihydrate having about 6.5% to about 7.5% (w/w) of water as depicted in KF.

8. The solid state form of Apalutamide according to claim 5, wherein crystalline form T2 is a 2-butanol solvate.

9. A solid state form of Apalutamide according to claim 1, which is polymorphically pure.

10. A pharmaceutical composition or formulation comprising a solid state form of Apalutamide or combinations thereof according to claim 1.

11. A pharmaceutical composition or formulation according to claim 10 comprising at least one pharmaceutically acceptable excipient.

12. A process for preparing a pharmaceutical composition or formulation according to claim 10 comprising combining any one or combination of the solid state forms of Apalutamide and at least one pharmaceutically acceptable excipient.

13. A process for preparing other solid state forms of Apalutamide comprising preparing any one or combination of the solid state forms of Apalutamide according to claim 9 and converting them to other crystalline forms of Apalutamide.

14. A method of treating prostate cancer, comprising administering a therapeutically effective amount of any one or combination of the solid state forms of Apalutamide according to claim 1 to a subject suffering from prostate cancer, or otherwise in need of the treatment.

15. A pharmaceutical composition or formulation comprising a solid state form of Apalutamide or combinations thereof according to claim 2.

16. A pharmaceutical composition or formulation according to claim 15 comprising at least one pharmaceutically acceptable excipient.

17. A process for preparing a pharmaceutical composition or formulation according to claim 15 comprising combining any one or combination of the solid state forms of Apalutamide and at least one pharmaceutically acceptable excipient.

18. A method of treating prostate cancer, comprising administering a therapeutically effective amount of any one or combination of the solid state forms of Apalutamide according to claim 2 to a subject suffering from prostate cancer, or otherwise in need of the treatment.

* * * * *